United States Patent
Ochi et al.

(10) Patent No.: US 10,548,633 B2
(45) Date of Patent: Feb. 4, 2020

(54) VIDEO NEEDLE SYRINGE

(71) Applicant: Nanosurgery Technology Corporation, Sarasota, FL (US)

(72) Inventors: Sam Seiichiro Ochi, Lakewood Ranch, FL (US); Mark Walter, Sarasota, FL (US)

(73) Assignee: Nanosurgery Technology Corporation, Sarasota, FL (US)

( * ) Notice: Subject to any disclaimer, the term of this patent is extended or adjusted under 35 U.S.C. 154(b) by 413 days.

(21) Appl. No.: 15/444,180

(22) Filed: Feb. 27, 2017

(65) Prior Publication Data

US 2017/0245890 A1    Aug. 31, 2017

Related U.S. Application Data

(60) Provisional application No. 62/300,714, filed on Feb. 26, 2016.

(51) Int. Cl.
| | |
|---|---|
| A61B 1/015 | (2006.01) |
| A61B 1/05 | (2006.01) |
| A61B 17/00 | (2006.01) |
| A61B 17/34 | (2006.01) |
| A61B 1/00 | (2006.01) |
| A61B 1/07 | (2006.01) |
| A61B 1/317 | (2006.01) |

(52) U.S. Cl.
CPC ........ *A61B 17/3478* (2013.01); *A61B 1/0008* (2013.01); *A61B 1/00009* (2013.01); *A61B 1/00045* (2013.01); *A61B 1/00078* (2013.01); *A61B 1/015* (2013.01); *A61B 1/051* (2013.01); *A61B 1/07* (2013.01); *A61B 1/317* (2013.01); *A61B 2017/00367* (2013.01); *A61B 2017/346* (2013.01); *A61B 2017/3456* (2013.01)

(58) Field of Classification Search
CPC .............. A61B 1/0008; A61B 1/00135; A61B 1/00154; A61B 1/012; A61B 1/015; A61B 1/05; A61B 1/051; A61B 1/07; A61B 1/126; A61B 17/3478; A61M 5/3213
See application file for complete search history.

(56) References Cited

U.S. PATENT DOCUMENTS

| | | | | |
|---|---|---|---|---|
| 5,385,572 | A * | 1/1995 | Nobles | A61B 1/042 604/264 |
| 6,387,043 | B1 * | 5/2002 | Yoon | A61B 1/00052 600/104 |
| 7,837,724 | B2 | 11/2010 | Keeble et al. | |
| 7,927,272 | B2 * | 4/2011 | Bayer | A61B 1/00154 600/107 |

(Continued)

FOREIGN PATENT DOCUMENTS

WO    WO 2015/200712 A1    12/2015

OTHER PUBLICATIONS

International Search Report and Written Opinion for PCT/US2017/019768 dated Jun. 7, 2017.

*Primary Examiner* — John P Leubecker

(57) ABSTRACT

An imaging needle apparatus includes a body, a needle coupled to the body, a probe, and an imager. The needle includes a needle body and a sharp tip. The probe can be exposed from the needle or housed within the needle body according to an operation being performed with the image needle apparatus. The imager is disposed inside of the probe, and includes a plurality of photocells.

15 Claims, 22 Drawing Sheets

(56) References Cited

U.S. PATENT DOCUMENTS

| | | | |
|---|---|---|---|
| 8,821,387 B2 | 9/2014 | Kucklick et al. | |
| 2003/0163029 A1* | 8/2003 | Sonnenschein | A61B 1/0005 600/160 |
| 2005/0004453 A1 | 1/2005 | Tearney et al. | |
| 2006/0209292 A1* | 9/2006 | Dowski, Jr. | G02B 3/0056 356/121 |
| 2010/0274081 A1* | 10/2010 | Okoniewski | A61B 17/3474 600/109 |
| 2011/0245605 A1* | 10/2011 | Jacobsen | A61B 1/015 600/109 |
| 2011/0261183 A1* | 10/2011 | Ma | A61B 90/361 348/77 |
| 2011/0313255 A1* | 12/2011 | Stanley | A61B 1/3132 600/205 |
| 2014/0135809 A1* | 5/2014 | Robertson | A61M 29/02 606/191 |
| 2015/0031946 A1* | 1/2015 | Saadat | A61B 1/05 600/104 |
| 2015/0173592 A1* | 6/2015 | Leeflang | A61B 17/3478 600/106 |
| 2015/0342621 A1* | 12/2015 | Jackson, III | A61B 5/6878 600/546 |
| 2016/0243343 A1* | 8/2016 | Miller | A61M 25/10182 |
| 2017/0042573 A1* | 2/2017 | Savvouras | A61B 17/3474 |
| 2017/0086666 A1* | 3/2017 | Kienzle | A61B 1/00066 |

\* cited by examiner

VIDEO NEEDLE SYRINGE

CROSS REFERENCE TO RELATED APPLICATIONS

This application claims the benefit of U.S. Provisional Patent Application No. 62/300,714, filed on Feb. 26, 2016, which is incorporated by reference herein for all purposes.

BACKGROUND

The present disclosure relates to a bee-eye imager apparatus, a method for fabricating a bee-eye imager apparatus, and a video needle syringe.

Traditional surgical procedures are open procedures. In an open surgical procedure, a surgeon makes a large incision on a patient in order to view and correct physical ailments using surgical tools. Open procedures have several drawbacks. The large surgical incisions used to perform open procedures can become infected. Surgeons may damage surrounding tissues during open procedures, while trying to manipulate the surgical site. Open procedures often require patients to undergo full anesthesia, which independently increases risks of death and/or serious complications. In addition, open procedures can cause patients severe discomfort during recovery periods.

In order to avoid the complications of open procedures, surgeons have developed minimally invasive surgical techniques to perform surgeries that were traditionally performed as open procedures. In contrast to open procedures, minimally invasive procedures can be performed by inserting surgical tools through small incisions in a patient's skin. Minimally invasive procedures have various advantages over open procedures, including lower infection risks, lower patient discomfort, and lower anesthesia requirements.

The small incisions used in minimally invasive procedures make viewing the surgical field difficult. Accordingly, surgeons generally use imaging devices, e.g., endoscopes, during minimally invasive procedures in order to indirectly view the surgical field. Some of these imaging devices must be inserted into a patient's body through the small incisions.

Arthroscopy is a type of minimally invasive orthopedic procedure performed in a skeletal joint cavity. An arthroscope includes a camera that may be inserted directly into a skeletal joint. With help from the arthroscope, surgeons can diagnose various problems related to the skeletal joint.

In certain cases, arthroscopes can be used to determine whether a therapeutic material should be delivered to the skeletal joint. For example, a surgeon may use an arthroscope to determine whether to deliver a drug, stem cells, or anesthesia for a future procedure to the skeletal joint. Some of these therapeutic materials can be injected using a syringe and a needle.

The cameras used in medical applications, such as those used in arthroscopes, should be precise and have high resolution. However, traditional high-resolution imaging modalities may be expensive. Furthermore, these imaging modalities may be bulky, and unsuitable for certain applications.

SUMMARY

The present disclosure relates to an imaging needle apparatus and a bee eye imager.

In an embodiment, an imaging needle apparatus includes a body; a needle coupled to the body, the needle including a needle body and a sharp tip; a probe including a blunt tip that can be exposed from the needle or housed within the needle according to an operation being performed with the image needle apparatus; and an imager disposed inside of the probe, the imager including a plurality of photocells.

The needle body may be hollow, and the probe may be disposed inside of the needle body.

The body may be configured to exert a pressure in a space inside of the probe, and the probe may be completely housed within the needle body.

The body may include a syringe configured to exert the pressure in the space.

The probe may have a plurality of side ports, which are holes through a side of the probe. When the body exerts the pressure on fluid inside of the probe space, the fluid may be emitted through the side ports.

The probe may have a plurality of lumens, which are holes through the blunt tip of the probe. When the body exerts the pressure on the fluid inside of the probe space, the fluid may be emitted through the lumens.

The apparatus may further include a lens assembly disposed inside of the probe, the lens assembly including a plurality of lenses respectively focusing light on the plurality of photocells of the imager, the lens assembly comprising a Fresnel lens; and a plurality of illumination light pipes extending along an outer surface of the imager and an outer surface of the lens assembly, the plurality of illumination light pipes transmitting light through the blunt tip of the probe.

The apparatus may further include a bundle disposed inside the probe, the bundle including a cable, wherein the imager includes an imager chip and a stack of integrated circuits (ICs) coupled to the imager chip, the imager chip including the plurality of photocells arrayed in a grid, the stack of ICs processing imaging signals from the photocells of the imager, the cable transmitting the processed imaging signals from the stack of ICs.

The body may include a port, the port being coupled to the cable.

The blunt tip of the probe may be transparent.

The blunt tip of the probe may be retractable from the sharp tip of the needle.

The apparatus may further include a control mechanism provided on the body, the control mechanism having a first state and a second state, wherein the blunt tip is retracted to be housed within the needle body when the control mechanism is in the first state, the blunt tip is extended from the needle and exposed when the control mechanism is in the second state.

The control mechanism may include a plurality of fins extending from the body, the plurality of fins being configured to rotate in a circumferential direction.

In an embodiment, a system comprises an imaging needle apparatus and a display. The imaging needle apparatus may include a body; a needle coupled to the body, the needle including a needle body and a sharp tip; a probe including a blunt tip that can be exposed from the needle or housed within the needle according to an operation being performed with the imaging needle apparatus; and an imager disposed inside of the probe, the imager including a plurality of photocells. The display may display an image based on the imaging signal.

The needle may be hollow, the probe being disposed inside of the needle body.

The body may include a syringe configured to exert a pressure in a space inside of the probe.

The probe may have a plurality of side ports and a plurality of lumens, the side ports being holes through a side of the probe, the lumens being holes through the blunt tip of the probe, when the syringe body exerts a pressure on a fluid in the space, the fluid may be emitted through the side ports and the lumens.

The system may further include a lens assembly disposed inside of the probe, the lens assembly including a plurality of lenses respectively focusing light on the plurality of photocells of the imager; a plurality of illumination light pipes extending along an outer surface of the imager and an outer surface of the lens assembly, the plurality of illumination light pipes transmitting light through the blunt tip of the probe, wherein the imager includes an imager chip and a stack of integrated circuits (ICs) coupled to the imager chip, the imager chip including the plurality of photocells arrayed in a grid, the stack of ICs processing imaging signals from the photocells of the imager.

The imaging needle apparatus may further include a control mechanism provided on the body, the control mechanism having a first state and a second state, wherein the blunt tip is retracted to be housed within the needle body when the control mechanism is in the first state, the blunt tip is extended from the needle and exposed when the control mechanism is in the second state.

The control mechanism may include a plurality of fins extending from the body, the plurality of fins being configured to rotate in a circumferential direction.

BRIEF DESCRIPTION OF THE DRAWINGS

FIG. 16 illustrates a detail view of a bee-eye imager pixel according to an embodiment.

FIG. 17 illustrates a detail view of a bee-eye imager pixel according to an embodiment.

DETAILED DESCRIPTION

Figure 1:
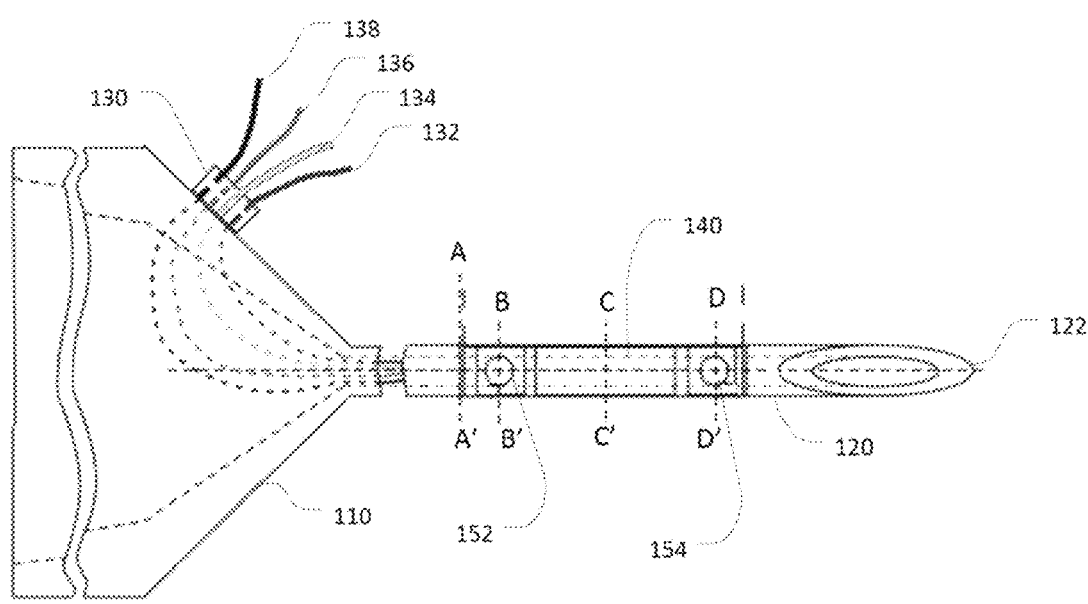
FIG. 1 illustrates an imaging apparatus according to an embodiment.

A detailed description of embodiments is provided below along with accompanying figures. The scope of this disclosure is limited only by the claims and encompasses numerous alternatives, modifications and equivalents. Although steps of various processes are presented in a particular order, embodiments are not necessarily limited to being performed in the listed order. In some embodiments, certain operations may be performed simultaneously, in an order other than the described order, or not performed at all.

Numerous specific details are set forth in the following description in order to provide a thorough understanding of the present disclosure. These details are provided for the purpose of example and embodiments may be practiced according to the claims without some or all of these specific details. For the purpose of clarity, technical material that is known in the technical fields related to this disclosure has not been described in detail so that the disclosure is not unnecessarily obscured.

The present disclosure relates to an imaging needle apparatus and a bee-eye imager. The imaging needle apparatus can take pictures, or video, or both using an image capturing device or imager. The image capturing device or imager may be proximately located to a needle, or inside of the needle. In an embodiment, the apparatus is a video syringe and is capable of capturing images and injecting fluid into a desired location, e.g., at a knee or shoulder joint of a person. In an embodiment, the fluid may be stem cell fluid, drugs, or other fluid used for medical treatment. The imaging needle apparatus may capture images and/or video using the bee-eye imager.

In an embodiment, the bee-eye imager includes a lens system that has a concave configuration globally and a convex configuration locally. The lens system may use the Fresnel lens concept for each lens focused onto an individual pixel center. The global concave nature of the lens system allows for a large field of view, for example, greater than 60 degrees along at least one axis. The concave nature of the individual lens allows for an approximate focusing distance, such as about 100 micrometers. Below are some of the concepts associated with the lens system according to an embodiment.

An image may be restricted from an individual lens to a photocell area in an individual pixel. For example, a 7.5 micrometer diameter individual lens may restrict light to a 2 um diameter light sensitive photocell area of an 8 micrometer by 8 micrometer pixel. The focus of the lens may be within the photocell area. Any light that goes through the lens and falls outside the photocell area may not affect this light sensitive photocell.

The size of the light-sensitive photocell at the pixel center may be adjusted to increase resolution. The smaller the size of the photocell area, the greater the resolution. However, the efficiency of the light sensitive photocell diode may drop as the dimensions approach the wavelength of light at, for example, at 0.5 micrometers.

The resolution of the bee-eye imager may also depend on the focal length of the lens assembly. The resolution may increase as the focal length increases. Accordingly, the focal length of the bee-eye imager may be increased as size and space permits. The focal length may be adjusted to be greater than 100 micrometers, for example.

The lenses of the bee-eye imager may be focused to infinity. Accordingly, the bee-eye imager can be made without expensive and/or bulky lenses. The bee-eye imager can be built into small devices, such as imaging needles and drones the size of insects.

The bee-eye imager can be implemented using standard wafer stacking and 3D assembly technology, such as techniques used in the universal service bus (USB) memory industry. A top level of the bee-eye imager may be the lens assembly. The next level may be a light pipe assembly, which may have a thickness between 100 micrometers and 400 micrometers. The greater the thickness of the light pipe assembly, the greater the resolution. An imager chip may be disposed underneath the light pipe assembly. The imager chip may be a back-lit imager chip or a standard front-lit imager. The imager chip may include CMOS circuitry built adjacent to the photo diode cell to improve sensitivity and pre-processing, and to reduce complexity and power further down the image processing chain. Other configurations are also possible.

The imager chip may include circuitry that pre-processes captured images. The imager chip may have reduced power overhead to minimize power dissipation within the imager chip and circuitry surrounding the imager chip. The captured images may be converted to USB compatible data.

The pre-processing circuitry may be integrated into individual pixels, and may provide for image-stitching. A "mosaic image" may be generated by stitching images together so that a wider field of view is created as new image data is provided by the imager chip. This creates an image wider and greater than the imager chip could otherwise provide.

The bee-eye imager may be provided on a needle of a video syringe. As the needle of the video syringe moves toward its target and provides instantaneous image updates, each of the previous images may be retained in memory and processed to create a wider field of view. The video syringe may recognize that the data viewed is "still" with respect to itself. The subject area viewed is looked upon as stationary—except the information originating from the video syringe. Using processing circuitry in the bee-eye imager, components of an old frame can be reused in a new frame, when the components of the old frame are stationary with respect to new frame. An old image can be "morphed" to accommodate a new image. The video syringe may also take advantage of the fact that most of the movement of the needle may be vertical and not horizontal (with respect to the shaft of the needle). This may be somewhat like a "magic" paint brush that creates a picture as the brush is manipulated over a canvas.

A standardized image of an area being examined by the bee-eye imager may be displayed by a monitor with a current image and/or video frame, such that a user can compare features, e.g., color, shape, etc. In an embodiment, the images and/or video output by the bee-eye imager may be recorded.

Figure 2:
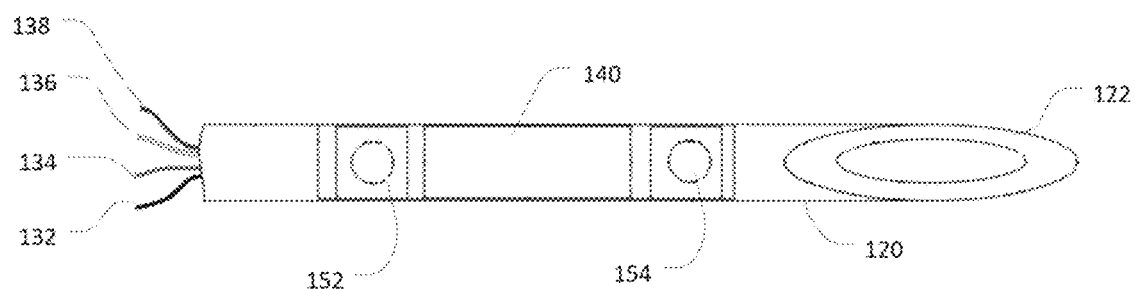
FIG. 2 illustrates a needle the imaging apparatus from a first side view according to an embodiment.
Figure 3:
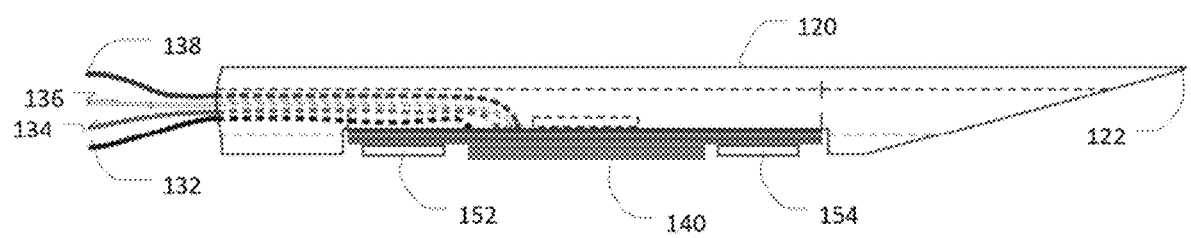
FIG. 3 illustrates the needle of the imaging apparatus from the second view according to an embodiment.

FIG. 1 shows an imaging apparatus 100 according to an embodiment of the present disclosure. The imaging apparatus 100 may include a syringe 110, a needle 120, a wire output 130, an imager 140, and first and second light-emitting diodes (LEDs) 152 and 154. FIGS. 2 and 3 illustrate the needle 120 from first and second side views according to an embodiment of the present disclosure.

The syringe 110 may be used to inject fluid through the needle 120. The syringe 110 may be hollow, and may stably house fluid before the fluid is injected through the needle 120. The syringe 110 may exert a positive pressure on the fluid in order to propel the fluid through the needle 120. The syringe 110 may push fluid in a direction that is parallel to the needle 120, such that the fluid can be propelled through the needle 120 with relatively laminar flow. That is, the position of the syringe 110 with respect to the needle 120 prevents fluids from turbulently flowing through the needle 120.

The syringe 110 may include a plunger or a pump that may propel the fluid through the needle 120. When the syringe 110 includes a plunger, a user can deliver fluid through the needle 120 by pushing the plunger toward the needle 120 in a direction parallel to the needle 120.

The needle 120 may include a sharp tip 122 that can pierce soft tissue. Although not illustrated, the sharp tip 122 may be configured to be retractable into the needle 120 so that the needle 120 would have a blunt tip (not shown) when the sharp tip 122 is retracted into the needle 120. In an embodiment, the needle 120 can pierce soft tissue around a skeletal joint, such as a knee.

As shown by FIG. 3, the tip 122 of the needle 120 may be tapered. The needle 120 may be a hypodermic needle. The tip 122 may be comprised of stainless steel. In an embodiment, an outer diameter of the needle may be between 0.0280 inches and 0.0285 inches, and an inner diameter of the needle may be between 0.0155 and 0.0175 inches. The needle 120 may be a 22-gauge hypodermic needle. In an embodiment, the needle 120 includes a flat outer surface attached to the imager 140. The imager 140 may be placed in other locations, e.g., on the front of the needle 120.

A fluid path may be provided within the needle 120 for fluid that may be injected into a specific site. The fluid may include, e.g., a fluid drug or stem cell fluid. When the syringe 110 increases pressure in the fluid path, the fluid can be emitted from the tip 122 of the needle 120.

In an embodiment, the needle 120 includes a first path for the wires and a second, separate path for injecting fluid. In another embodiment, the needle 120 has a single path shared by output wires from the imager 140 and the fluid.

The needle 120 may be attached or detached from the syringe 110. In an embodiment, the bayonet of the needle 120 may screw onto threads disposed on an attachment point of the syringe 110.

The wire output 130 may be coupled to one or more conductive wires that output imaging data from the imager 140. The wire output 130 may be further coupled to one or more wires that supply power to the imager 140. In other embodiments, however, fewer or additional wires may be coupled to the wire output 130.

The wire output 130 may be coupled to a battery, and may transfer power from the battery to the imager. In an embodiment, the wire output 130 transfers power to the imager from an external device, such as an external display device, via a wired or wireless connection.

The wire output 130 may include one or more processors that convert the imaging data from the imager 140 to a standard video format. In an embodiment, the wire output 130 receives imaging data from the imager 140. The imaging data may be in the standard video format, e.g., Universal Serial Bus (USB) or High-Definition Multimedia Interface (HDMI) compatible.

The wire output 130 may convert one or more of the wires transferring imaging data and/or power to and from the imager 140 into a single output wire. In an embodiment, the wire output 130 may output the one or more signal and power wires to a single socket or plug that may interface with an external display device. The socket or plug may be a USB or an HDMI socket or plug, or other communication interfaces. The external display device may thus display imaging data from the imager 140 and may power the imager 140 via the wire output 130.

In an embodiment, the imaging needle apparatus includes or is coupled to a communication component (not shown) that wirelessly transmits the imaging data to an external display device 1220 (see FIG. 12) using Bluetooth or Wi-Fi, or other wireless communication protocols.

Referring back to FIG. 1, four wires are coupled between the wire output 130 and the imager 140. The wires may include a positive power wire 132, a negative power wire 134, a positive data wire 136, and a negative data wire 138.

Each of the wires 132, 134, 136, and 138 may include a conductive material and an insulative material that covers the conductive material. In an embodiment, each wire has a diameter of about 75 µm. The wires may be color coded: for example, the positive power wire 132 may be red, the positive data wire 136 may be white, the negative data wire 138 may be green, and the negative power wire 134 may be black.

One or more of the wires 132, 134, 136, and 138 may be micro-coaxial wires, as discussed below with respect to FIGS. 8 through 11. In an embodiment, all of the wires 132, 134, 136, and 138 are integrated into a single micro-coaxial wire with a data bypass capacitor and a power supply bypass capacitor.

The wires 132, 134, 136, and 138 may protrude from the imager 140 into the interior of the needle 120. The wires 132, 134, 136, and 138 may be threaded within the interior of the needle 120, pass through a bayonet of the needle 120, and disposed in an interior space of the syringe 110, and attach to an interior side of the wire output 130. The wires 132, 134, 136, and 138 may be electrically coupled between the imager 140 and the wire output 130.

The imager 140 may be used to capture images and/or video of spaces and structures disposed in the vicinity of the needle 120. The imager 140 may capture images and/or video in one or more directions with respect to the needle 120. The imager 140 may, for example, capture images and/or video in a radial direction with respect to the needle 120. The imager 140 may output the images and/or video as imaging data.

The imager 140 may be fixed at a position proximate to the needle 120. For example, the imager 140 may be attached to an outer surface of the needle 120. The imager 140 may be attached to the outer surface of the needle 120 with an adhesive. In an embodiment, the imager 140 is fixed on an outside surface of the needle 120 at a position within ⅛ to ½ inches of the tip 122. In an embodiment, the imager 140 may be attached to a flat exterior surface of the needle 120.

In an embodiment, the imager 140 is a bee-eye imager including a plurality of complementary metal-oxide semiconductor (CMOS) pixels. The imager 140 may include a plurality of image sensors corresponding to a plurality of pixels. The image sensors may be a plurality of imaging chips disposed along a flat surface, for example.

The imager 140 may include one or more controllers coupled between the communication interface and the circuits in the rest of the imager 140. The imager 140 may further include analog and digital control electronics that convert imaging signals from the imager 140 to signals compatible with a communication interface. The imager 140 may include electronics that converts raw imaging data to imaging data that is compatible with the wire output 130 and/or external display device. For example, the imager 140 may convert the raw imaging data to uncompressed video imaging data compatible with a USB- or HDMI-based interface.

The imager 140 may output data to a first bypass capacitor that is coupled between the imager 140 and the positive and negative data wires 136 and 138. In addition, a second bypass capacitor may be coupled between the imager 140 and the positive and negative data wires 132 and 134. The first and second bypass capacitors may reduce noise in signals transmitted through the wires 132, 134, 136, and 138.

The first and second LEDs 152 and 154 may illuminate areas around the needle 120, in order to more easily capture high quality images using the imager 140. In an embodiment, one or both of the first and second LEDs 152 and 154 emits white light. The first and second LEDs 152 and 154 may be integrated into the imager 140. In an embodiment, the first and second LEDs 152 and 154 each emit light from a surface having an area of 680 μm by 680 μm.

In an embodiment, the first LED 152 may be located between the imager 140 and the syringe 130. The second LED may be located between the imager 140 and the tip 122 of the needle 120.

Although two LEDs are illustrated, embodiments are not so limited. The apparatus 100 may include more or fewer than two LEDs.

The imager 140 and the first and second LEDs 152 and 154 may be covered with a clear, biocompatible sealant (not shown). The sealant may fix the imager 140 and the first and second LEDs 152 and 154 onto the needle 120, such that components of the imager 140 and the first and second LEDs 152 and 152 do not become dislodged, e.g., by human tissue, when the imaging apparatus 100 is used during a medical procedure. In addition, the sealant may cover the imager 140 and the first and second LEDs 152 and 154 with a smooth surface, such that the needle 120 can be smoothly inserted into a desired site.

FIGS. 4 through 7 show cross sections of the needle 140 according to an embodiment of the present disclosure.

Figure 4:
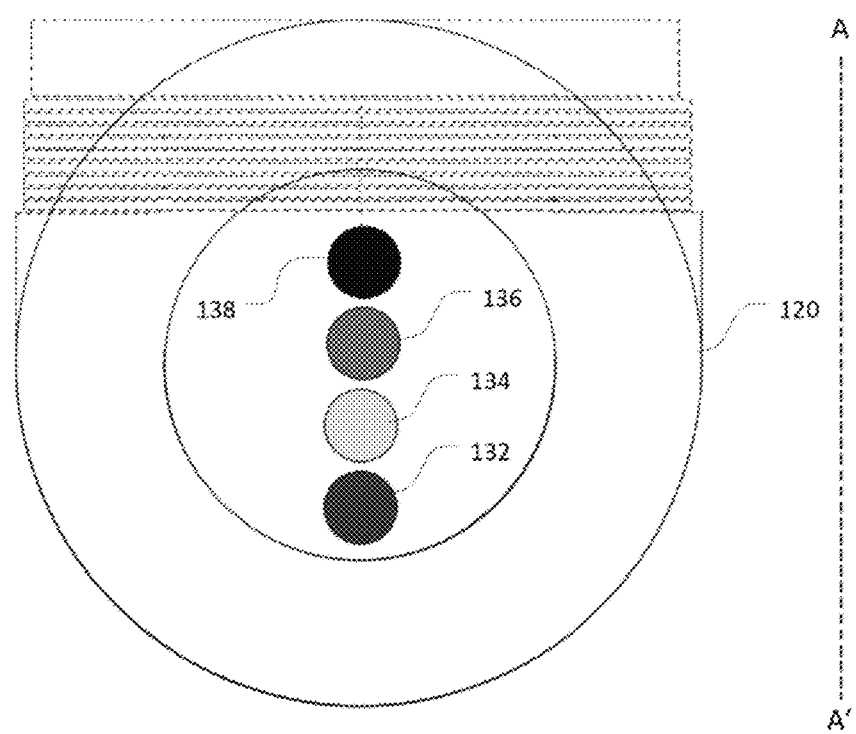
FIG. 4 illustrates a cross-section of the needle of the imaging apparatus along a line A-A' according to an embodiment.

FIG. 4 illustrates a cross section of the needle 120 between the syringe 130 and he imager 140 along a line A-A' illustrated in FIG. 1. FIG. 4 shows that the outer surface of the needle 120 may be rounded where the imager 140 is not present.

Figure 5:
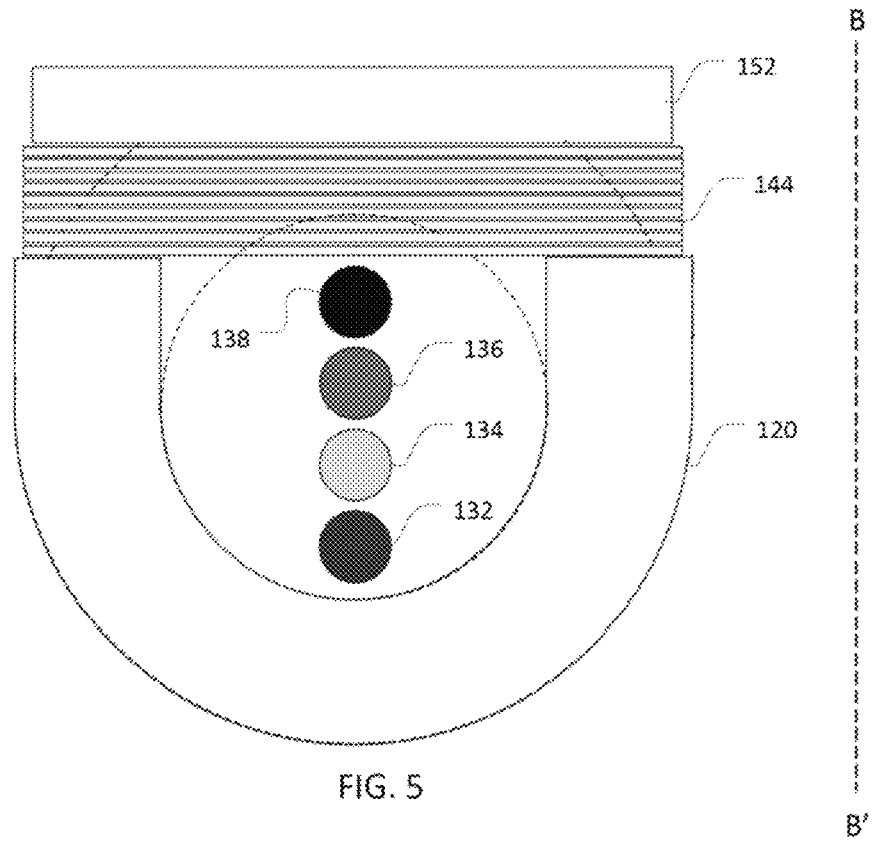
FIG. 5 illustrates a cross-section of the needle of the imaging apparatus along a line B-B' according to an embodiment.

FIG. 5 shows a cross section of the needle 120, the first LED 152, the imager 140, and the wires 132, 134, 136, and 138 along a line B-B' illustrated in FIG. 1.

The first LED 152 may be disposed on the imager 140. The first LED 152 may emit light in a direction that points away from the needle 120 and in an imaging direction of the imager 140.

The imager 140 may be disposed between the first LED and the needle 120. The imager 140 may include a plurality of stacked chips. The stacked chips of the imager 140 may include an imaging chip 142 and an integrated circuit (IC) stack 144. The IC stack 144 may include, for example, silicon CMOS circuits. Each stacked chip may have a thickness of approximately 10 μm or less. In an embodiment, one or more stacked chips are each 5-8 μm thick. The imaging chip 142 may be located on top of the stack of control ICs 144. The number of ICs in IC stack 144 may vary depending on the implementation.

The first and second LEDs 152 and 154 as well as the first stack, may be located above the second stack of the imager 140. That is, the first and second LEDs 152 and 154 may be stacked on the imaging chip 142.

In an embodiment, the first LED 152 and the imager 140 are flat structures and may be attached to an outer surface of the needle 120. Accordingly, the device 100 may have a flat side where the imager 140 is attached to the outer surface of the needle 120, even though rest of the outer surface of the needle 120 may be curved.

In an embodiment, the outer corners of the imager 140 may be rounded, such that the needle 120 and the imager 140 together provide a round, elongated shape resembling a conventional, cylindrical needle. In an embodiment, one or more of control ICs in the imager 140 may fixed to an interior surface of the needle 120, such that the imager 140 may be partially disposed inside of the needle 120.

The wires 132, 134, 136, and 138 may extend from the imager 140 into the interior of the needle 120 and underneath the imager 140 and the first LED 152.

As shown in FIGS. 4 and 5, the wires 132, 134, 136, and 138 may have small cross-sectional areas compared to the interior of the needle, which may provide ample interior space for fluids to be injected from the tip 122 of the needle 120 with substantially laminar flow. In an embodiment, the cross-sectional area of the wires 132, 134, 136, and 138 may take up between 5 and 25% of the interior cross-sectional area of the needle 120.

In an embodiment, the wires 132, 134, 136, and 138 may be fixed to an interior surface of the needle 120, in order to provide a more continuous fluid path through the needle 120. The wires 132, 134, 136, and 138 may be glued to the interior surface of the needle 120.

Figure 6:
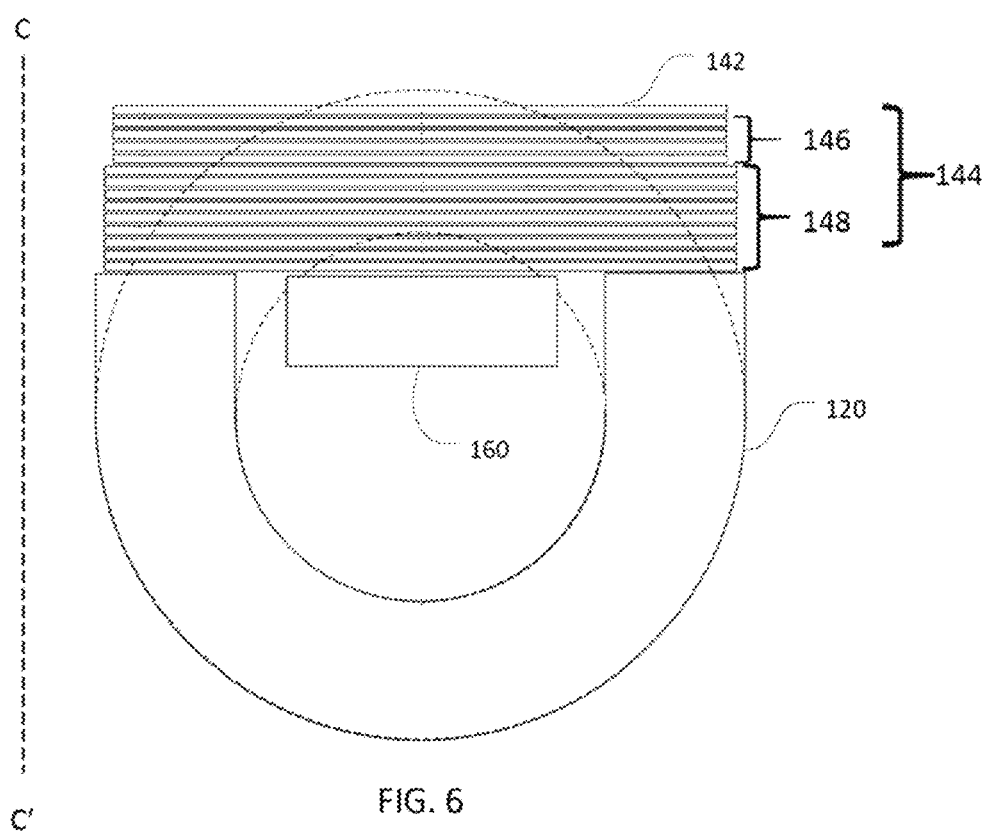
FIG. 6 illustrates a cross-section of the needle of the imaging apparatus along a line C-C' according to an embodiment.

FIG. 6 illustrates a cross-section of the needle 120, the imager 140, and a bypass capacitor 160 along a line C-C' according to an embodiment of the present disclosure. Specifically, FIG. 6 shows a cross-section of the imaging chip 142 and the IC stack 144 of the imager 140.

The imaging chip 142 may be disposed on top of the IC stack 144. The imaging chip 142 may include a plurality of imaging sensors corresponding to pixels. In an embodiment, the imaging chip 142 is a 1.36 mega pixel imager, and may include a 1 μm2 pixel array located over an area of 680 μm by 2000 μm on top of the IC stack 144.

The imaging chip 142 may convert image signals into electrical signals, and may pass the electrical signals to circuitry in the IC stack 144.

The IC stack 144 may include a plurality of ICs. In an embodiment, the plurality of ICs in the IC stack 144 may be divided into a first plurality of ICs in a first stack 146 and a second plurality of ICs in a second stack 148. Each of the plurality of ICs in the IC stack 144 may include a silicon wafer.

The first stack 146 may be stacked on top of the second stack 148, between the imaging chip 142 and the second stack 148. In an embodiment, the first stack 146 may include a stack of four CMOS ICs. In an embodiment, each of the CMOS ICs has a stacking surface with an area of a first size, for example, 680 μm by 2000 μm.

The second stack 148 may be disposed between the bypass capacitor 160 and the first stack 146. In an embodiment, the second stack 148 includes a first logic layer, a plurality of bit layers, and a second logic layer. The first logic layer (the "controller") may contain sense amps, write drivers, address decoders, and other elements that read and write memory bits. The plurality of bit layers may be stacked on the first logic layer. The second logic layer (the "I/O layer") may be attached underneath the controller and the plurality of bit layers. The I/O layer translates a signal from the controller according to a voltage and protocol that is understandable by an off-chip device, such as a processor, a field-programmable gate array (FPGA), an optical link, or other device.

In an embodiment, the second stack 148 may include 9 CMOS ICs. In an embodiment, each of the CMOS ICs has a stacking surface with an area of a second size that is larger than the first size, for example, 710 μm by 4000 μm. Alternatively, the second stack 148 may include 9 CMOS ICs that may each have a surface with an area of 700 μm by 4000 μm.

The second stack 148 may therefore have a larger width than the first stack 146 and the imaging chip 142. In addition, the second stack 148 may have a larger length than the first stack 146 or the imaging chip 142. Accordingly, the outer surface of the imager 140 may have slightly rounded edges, so that the needle 120 may be smoothly inserted into a desired surgical site.

In an embodiment, the first stack 146 and the imaging chip 142 may have substantially the same height as each of the first and second LEDs 152 and 154. A surgical-grade material may be disposed between the first stack 146 and the imaging chip 142 and the first and second LEDs 152 and 154, so that the apparatus 100 has a smooth outer surface.

The plurality of ICs in the IC stack 144 may be interconnected by through silicon vias (TSVs) and contacts. In some embodiments, the IC stack 144 and the imaging chip 142 may include copper TSVs and contacts. Alternatively or additionally, the IC stack 144 and the imaging chip 142 may include tungsten TSVs and contacts.

Tungsten TSVs and contacts provide a number of advantages over copper TSVs and contacts. Advantages of ICs with tungsten include better thermal compatibility, size, and density than ICs with copper alone.

Tungsten is more thermally compatible with silicon than copper. Tungsten and silicon have similar coefficients of thermal expansion. Accordingly, tungsten TSVs and contacts apply limited physical distress on surrounding a silicon wafer during operating conditions.

In addition, tungsten structures may be smaller than copper structures, and may therefore may have almost negligible inductance, capacitance, and resistance. Accordingly, tungsten contacts may be more cheap and reliable than copper contacts. For example, the tungsten contacts in the IC stack 144 may fill a 10 μm deep hole with a 10:1 aspect ratio. In an embodiment, the tungsten TSVs can have diameters of 1 μm or less, even with a 10:1 aspect ratio limit, when a wafer thickness is 10 μm or less. In an embodiment, the tungsten contacts may also be 1 μm (or less) wide, and arrayed on a 2 μm or smaller pitch (the center to center distance between repeated objects). Thus, embodiment of the IC stack 144 may include tungsten TSVs and contacts instead of larger copper through silicon vias (TSVs).

In contrast, copper TSVs may have a larger width than tungsten TSVs. For example, the copper TSVs in the IC stack 144 may be 5 μm wide and located on a 40 to 50 μm pitch. Copper is less thermally compatible with silicon than tungsten. That is, copper has a different thermal coefficient of expansion than silicon.

Tungsten can also be used to fabricate a more densely connected IC than copper alone. In an embodiment, a wafer in the IC stack 144 includes 5 μm wide copper TSVs spaced on a grid of 40 or more μm per step, and may alternatively or additionally include tungsten contacts can be organized on a pitch that is about two times the contact diameter, (e.g. 0.6 μm wide contacts can be on a 1.2 μm pitch, and 1 μm wide contacts can be on a 2 μm pitch). Thus, the tungsten contacts in the IC stack 144 may be made with very small diameters, and can also be arrayed on a very tight pitch. Thus, tungsten TSVs and contacts support a higher vertical interconnect per unit area across the surface of each wafer in the IC stack 144 than copper TSVs and contacts, and therefore support higher interconnect.

In an embodiment, the wafers of the IC stack 144 include only tungsten TSVs or contacts, or only a limited number of copper TSVs and contacts. In an embodiment, when a wafer of the IC stack 144 includes too much copper, a normal temperature change can break the wafer. Even if the die or wafer does not break, if a transistor is located too close to the copper TSV, the expansion or contraction of the copper can change the operating characteristics of the transistor, and may make the rest of the IC non-functional.

Due to high vertical interconnect from tungsten and copper TSVs and contacts, it is possible to perform potent and comprehensive post-assembly repair of the ICs in the IC stack 144. In an embodiment, a variety of redundant circuit elements are available, including spare contacts. In addition, redundant elements from one die may be used to repair defects in another die in the IC stack 144. The IC stack 144 may become more reparable by adding more dies to the stack.

That is, because the IC stack 144 may include small tungsten TSVs rather than large copper TSVs as vertical interconnects, the IC stack 144 may support post-assembly repair. Connections throughout the IC stack 144 may be located in precise locations, and there may be enough connections to do thorough post-assembly repair. Thus, the IC stack 144 of the imager 140 may include a memory subsystem that has high density, performance, and that operates under low power.

The bypass capacitor 160 may be disposed underneath the imager 140 inside of the interior space of the needle 120. The bypass capacitor 160 may be coupled between the second stack 148 of the imager 140 and the wires 132, 134, 136, and 138, and may reduce noise in imaging data transmitted by the positive data wire 136 and the negative data wire 138. One terminal of the bypass capacitor 160 may be connected to the positive data wire 136, and a second terminal of the bypass capacitor 160 may be connected to the negative data wire 138.

The bypass capacitor 160 may be of a 0201 size, leaving a cross sectional area for injected fluids within the interior of the needle 120. Fluids may flow through the needle 120, unimpeded by the imager 140 including the first and second stacks.

In an embodiment, another bypass capacitor may be disposed underneath the imager 140, and may also reduce noise in power supplied to the imager 140 through the positive power wire 132 and the negative power wire 134. The other bypass capacitor can be coupled between the positive power wire 132 and the negative power wire 134.

Embodiments of the apparatus 100 may be manufactured at a low cost. As such, the apparatus 100 can be a single use, disposable device. The video syringe can be a cost-effective alternative to conventional arthroscopes, for example.

The control ICs among the IC stack 144 and the imaging chip 142 may be manufactured using one or more of the following manufacturing methods.

A high performance CMOS process may be used to build high performance logic circuits in the imager 140, such as sense amps, write drivers, and decoders. A dynamic random-access memory (DRAM) process can be used to build memory storage bits in the imager 140. Larger feature-size processes can be used when they offer the right capabilities at a good cost, and more expensive, advanced processes can be used when they are needed. This mix of cheaper and more expensive processes can be used to build a single, highly optimized device.

Embodiments of the imaging needle apparatus include one or more wires that connect an imager to external electronics, such as a display apparatus. As noted above, in order to reduce the effect of noise across the one or more wires, each of the wires may be coupled to the bypass capacitor 160. In an embodiment, each wire is a micro-coaxial wire, in which the bypass capacitor is incorporated into the wire itself.

Figure 7:
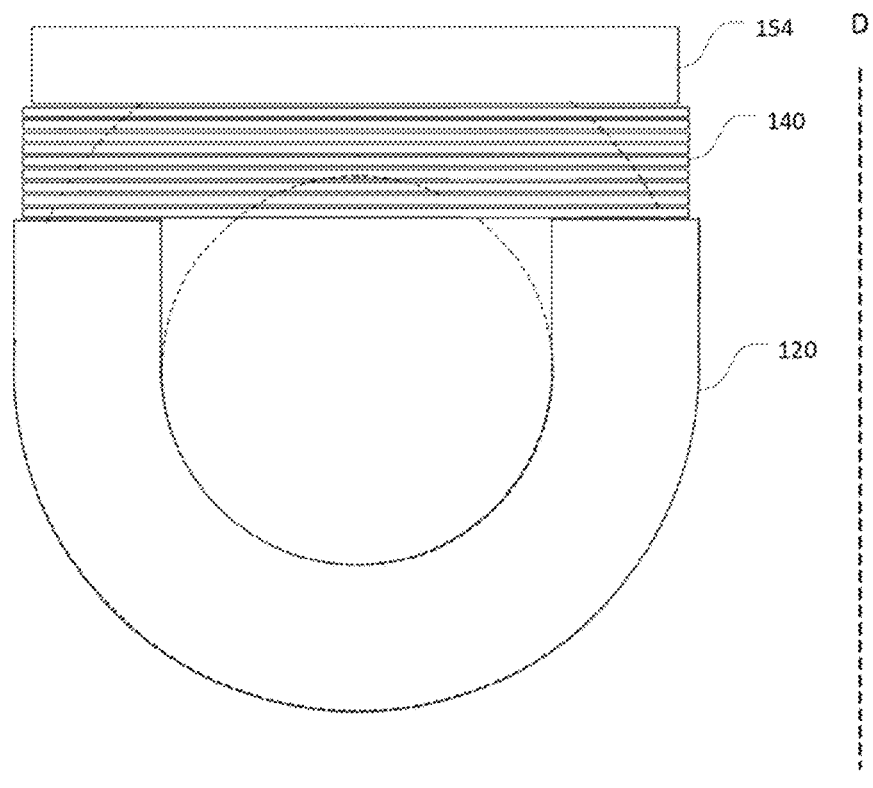
FIG. 7 illustrates a cross-section of the needle of the imaging apparatus along a line D-D' according to an embodiment.

FIG. 7 illustrates a cross-section of the needle 120, imager 140, and the first LED 154 along a line D-D' illustrated in FIG. 1.

Figure 8:
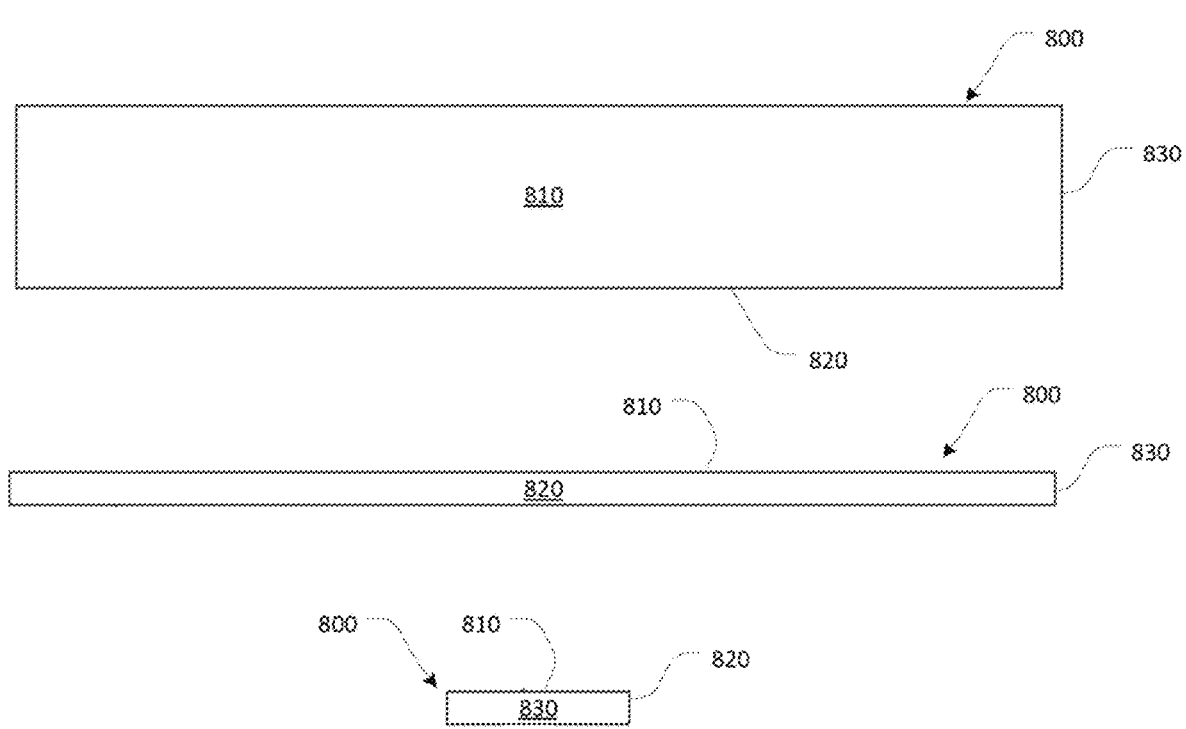
FIG. 8 illustrates a top view, a left or right side view, and a lower side view of a bee-eye imager according to an embodiment.

FIG. 8 illustrates a top view, a left or right side view, and a lower side view of a bee-eye imager 800, according to an embodiment. The bee-eye imager 800 may have the shape of a rectangular prism.

The bee-eye imager 800 may include a first side 810, a second side 820, and a third side 830. The first side 810 may point radially from a structure on which the bee-eye imager 800 is mounted, and may receive light to be imaged. In an embodiment, the first side 810 has a length of 4 mm, and a width of 0.7 mm.

The second side 820 may be perpendicular to the first side 810. In an embodiment, the second side has a length of 4 mm and a width of 126 micrometers.

The third side 830 may be perpendicular to the first side 810 and the second side 820. In an embodiment, the third side 830 has a length of 0.7 mm and a width of 126 micrometers.

Figure 9:
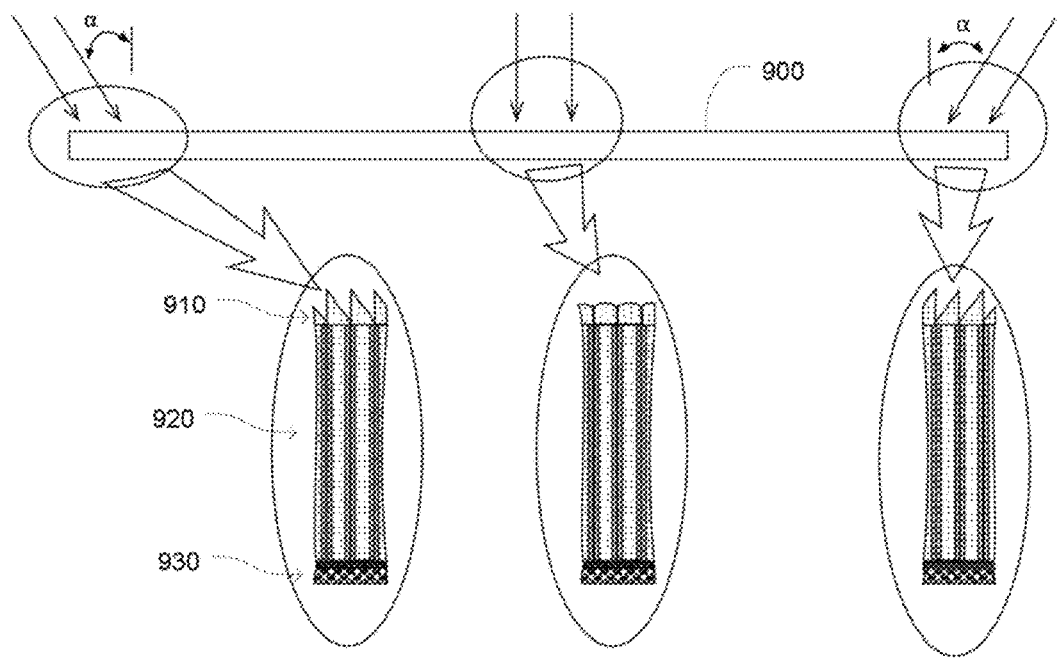
FIG. 9 illustrates a side view and partial cross sections of a bee-eye imager according to an embodiment.

FIG. 9 illustrates a side view and partial cross sections of a bee-eye imager 900, according to an embodiment. The bee-eye imager 200 may include a lens assembly 910, a light pipe assembly 920, and an imager chip 930.

The lens assembly 910 may capture light incident on the bee-eye imager 900, and may output the captured light to the light pipe assembly 920. The lens assembly 910 may include a plurality of lenses. An edge of the lens assembly 910 may capture incident light at an angle α with respect to a normal direction of a surface of the bee-eye imager 900. In an embodiment, the angle α may be 32 degrees.

The light pipe assembly 920 may channel light from the lens assembly 910 to the CMOS imager chip 930. The light pipe assembly 920 may include a plurality of light pipes respectively coupled to the plurality of lenses in the lens assembly 910.

The imager chip 930 may convert the light from the light pipe assembly 920 into an image, such as a digital image. The imager chip 930 may include a plurality of pixels respectively corresponding to the plurality of light pipes in the light pipe assembly 930. The imager chip 930 may be a CMOS imager chip.

Figure 10:
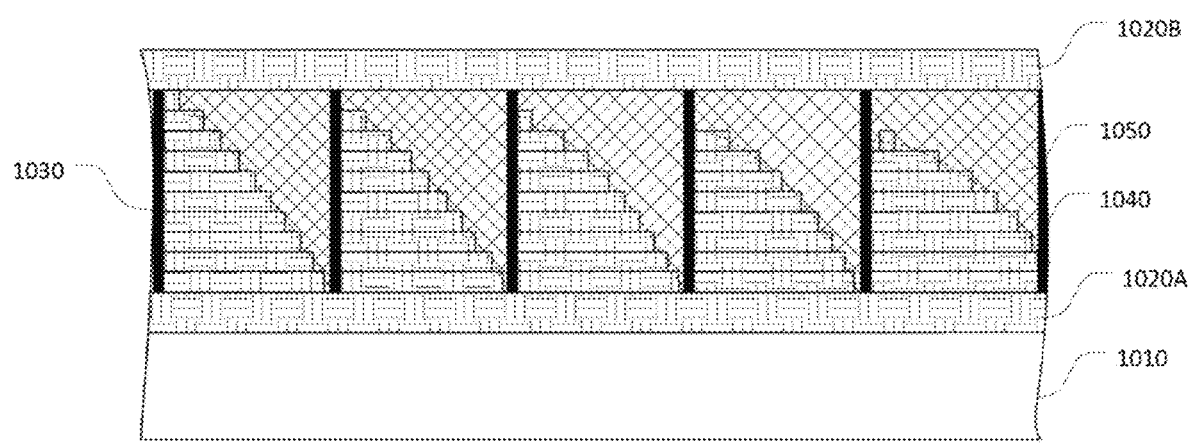
FIG. 10 illustrates a cross section of a bee-eye imager according to an embodiment.

FIG. 10 illustrates a cross section of a bee-eye lens assembly, according to an embodiment. The bee-eye lens assembly may include a substrate 1010, a first outer layer 1020A, cell boundaries 1030, lenses 1040, filler 1050, and a second outer layer 1020B.

The substrate 1010 may be a sacrificial substrate. In an embodiment, the substrate 1010 is a planarized silicon wafer.

The first outer layer 1020A may be disposed between a plurality of cells and the substrate 1010. The first outer layer 1020A may extend across the substrate 1010, and may include a first transparent material. The first transparent material may be silicon oxide, for example. In an embodiment, the first outer layer 1020A may have a thickness of 2 micrometers.

The cell boundaries 1030 may separate the plurality of cells from one another, and may extend from the first outer layer 1020A to the second outer layer 1020B. The cell boundaries 1030 may include an optically opaque material, such as poly silicon. The optically opaque material may have a granular surface to minimize optical reflections. In an embodiment, the cell boundaries 1030 may be separated by 8 micrometers, and may each extend 10 micrometers from the first outer layer 1020A to the second outer layer 1020B.

The lenses 1040 may be respectively disposed in the plurality of cells, and may each include a plurality of layers. The lenses 1040 may each include a base layer disposed next to the first outer layer 1020A, and progressively smaller layers stacked on the base layer. In an embodiment, each lens 1040 includes 11 or fewer layers that are each 1 micrometer thick. The lenses 1040 may include a second transparent material. In an embodiment, the second transparent material is silicon dioxide.

A first side of each lens 1040 may be disposed against one of the cell boundaries 1030. Accordingly, another side of each lens 1040 may have a specific curvature defined by the progressively smaller layers.

The lenses 1040 in the lens assembly may transmit and bend light due to the curvature. Different lenses 1040 in the lens assembly may have different curvatures. For example, lenses 1040 located at an outer edge of the lens assembly may bend light at a greater angle than lenses 1040 located at a center of the lens assembly.

The fillers 1050 may fill a negative space around the lenses 1040 in each of the cells defined by the cell boundaries 1030. The fillers 1050 may include a material that has a lower index of refraction than the lenses 1040 and the first and second outer layers 1020A and 1020B. The fillers 1050 may include silicon dioxide. The fillers 1050 may be sacrificial, such that they are etched and removed during a fabrication process in order to create voids or air pockets around the lenses 1040.

The second outer layer 1020B may extend across the cells defined by the cell boundaries 1030. The second outer layer 1020B may include the same material as the first outer layer 1020A.

FIGS. 11A through 11I illustrate fabrication steps of a bee-eye imager, according to an embodiment.

Figure 11A:
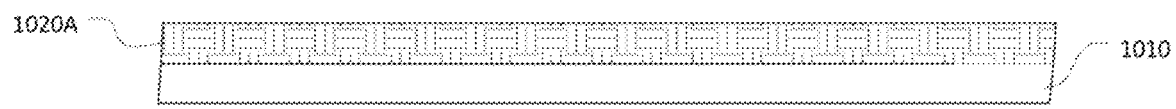
FIGS. 11A through 11I illustrate fabrication steps of a bee-eye imager according to an embodiment.

In FIG. 11A, the substrate 1010 may be covered by the first outer layer 1020A. The substrate 1010 may be a planarized silicon wafer, and may be optically flat. The first outer layer 1020A may include a thermal oxide. In an embodiment, the first outer layer 1020A may be grown on the substrate 1010, to have a height of, for example, 2 micrometers.

The first outer layer 1020A may be subsequently polished, such that it is optically flat.

Figure 11B:
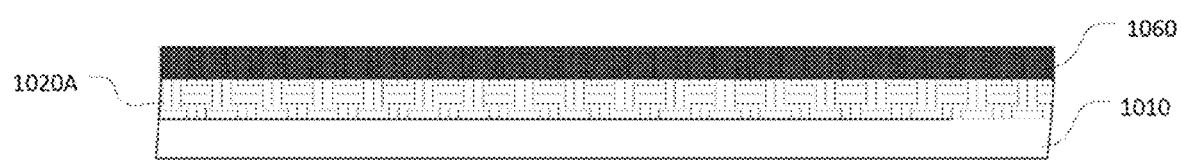

In FIG. 11B, a first photoresist layer 1060 may be deposited on the first outer layer 1020A. The first photoresist layer 1060 may be a lift-off photoresist layer.

Figure 11C:
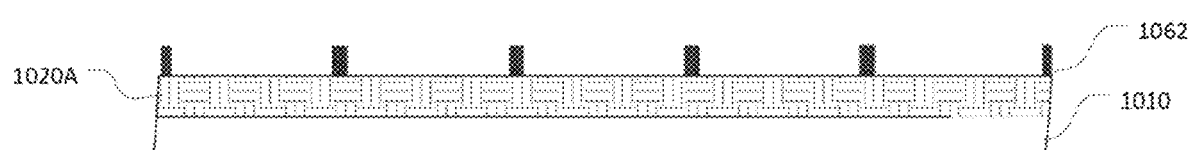

As illustrated in FIG. 11C, first photoresist patterns 1062 may be formed by etching the first photoresist layer 1060, thereby exposing an upper surface of the first outer layer 1020A at a plurality of positions between the first photoresist patterns 1062.

Figure 11D:
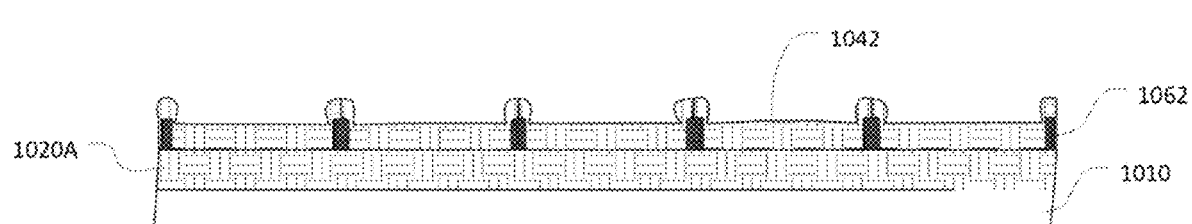

In FIG. 11D, a low-temperature silicon dioxide layer 1042 may be deposited over first photoresist patterns 1062 and on the exposed surface of the first outer layer 1020A. The silicon dioxide layer 1042 may be deposited via chemical vapor deposition. The silicon dioxide layer 1042 may correspond to the material of the lenses 1040.

Figure 11E:
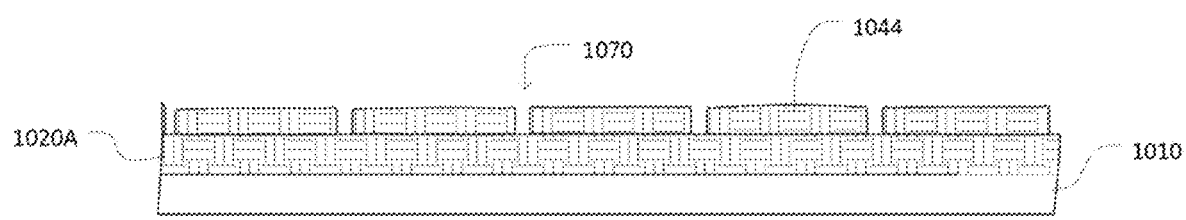

In FIG. 11E, the first photoresist patterns 1062 may be removed via a lift-off procedure. Excess portions of the silicon dioxide layer 1041 on top of the first photoresist patterns 1062 may also be removed, thereby forming base layers 1044. The base layers 1044 may be separated by first trenches 1070.

Figure 11F:
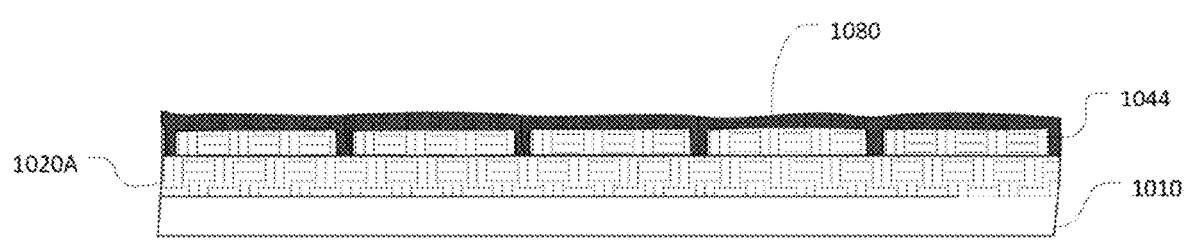

In FIG. 11F, a second photoresist layer 1080 may be deposited on the base layers 1044 and an upper surface of the first outer layer 1020A exposed by the first trenches 1070.

Figure 11G:
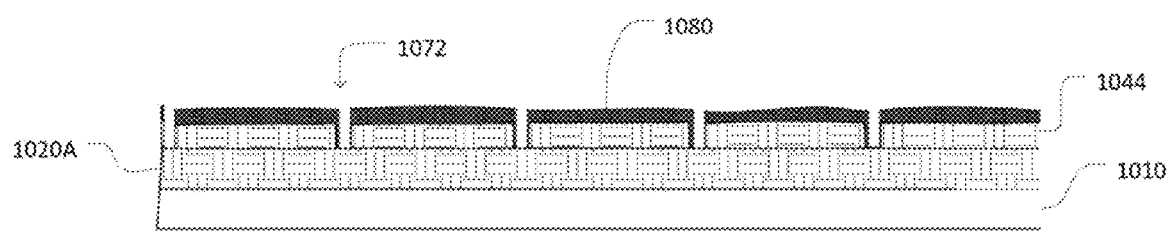

In FIG. 11G, second trenches 1072 may be etched into the second photoresist layer 1080 between the base layers 1044. The second trenches 1072 may expose the upper surface of the first outer layer 1020A.

Figure 11H:
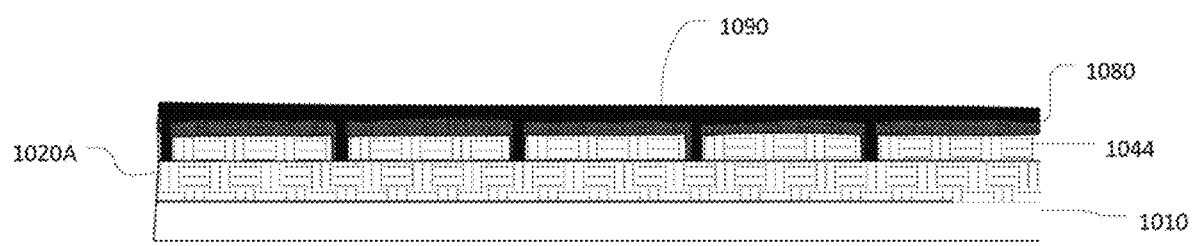

In FIG. 11H, an optically opaque material 1090 may be deposited over the second photoresist layer 1080, thereby filling the second trenches 1070 in the second photoresist layer 1080.

Figure 11I:
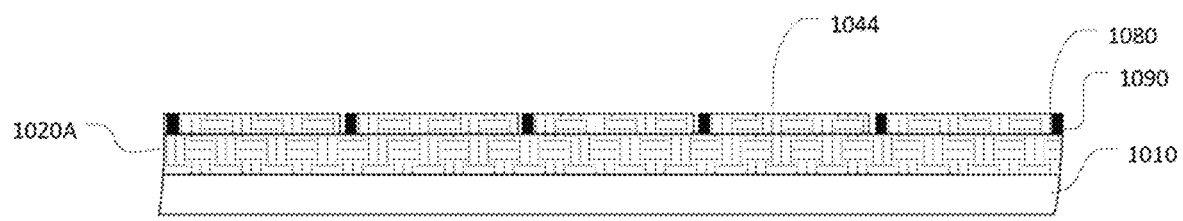

Subsequently, in FIG. 11I, the optically opaque material 1090, the second photoresist layer 1080, and the base layers 1044 may be planarized. The base layers 1044 may each have a height of about 1 micrometer. Upper surfaces of the sections of the base layers 1044 and the optically opaque material 1090 may be exposed. The remaining second photoresist layer 1080 may be removed.

In an embodiment, the preceding steps of FIGS. 11A through 11I may be repeated as necessary to create multiple stacked layers in cells of a lens assembly.

Figure 12:
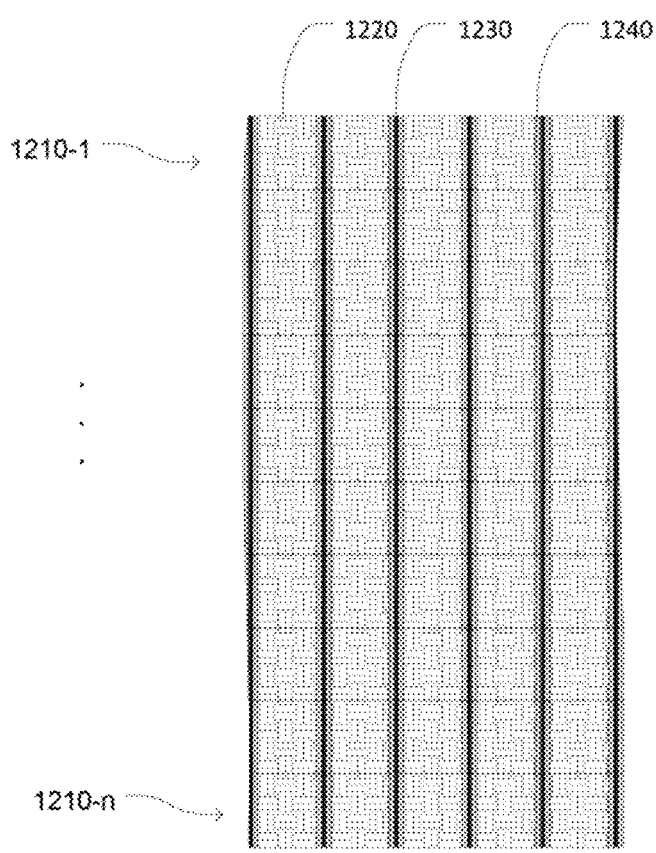
FIG. 12 illustrates a detail view of a bee-eye light pipe according to an embodiment.

FIG. 12 illustrates a detail view of a light pipe assembly, according to an embodiment. The light pipe assembly may include a plurality of light pipes that are optically isolated from one another.

Each light pipe may include a core material 1220 and a sheath material 1240. The core material 1220 may have a lower index of refraction than the sheath material 1040. In an embodiment, the sheath material 1240 may include a third material that has a greater index of refraction than the transparent materials of the first and second outer layers 1020A and 1020B, the lenses 1030, and the fillers 1050 described with respect to FIG. 10. In an embodiment, the core material 1220 includes silicon dioxide and the sheath material 1040 includes any of diamond, cubic zirconium (CZ), and zirconium oxide (ZrO2).

An isolation material 1230 may be disposed between each light pipe, and may include an optically opaque material. The isolation material 1230 between each light pipe substantially eliminates light passing through the sheath material of one pipe from leaking or passing into the adjacent pipe.

The core material 1220 and/or the sheath material 1240 may transmit light from a lens assembly to an imager. Light that hits an interface between the core material 1220 and the sheath material 1240 may pass through the light pipe unobstructed.

In an embodiment, each light pipe includes 10 layers of the core material 1220, the sheath material 1240, and/or the isolation material 1230. The layers may include layers of the core material 1220 that are 8 micrometers wide by 10 micrometers thick, and which are sandwiched between layers of the sheath material 1240 and the isolation material 1230.

Figure 13:
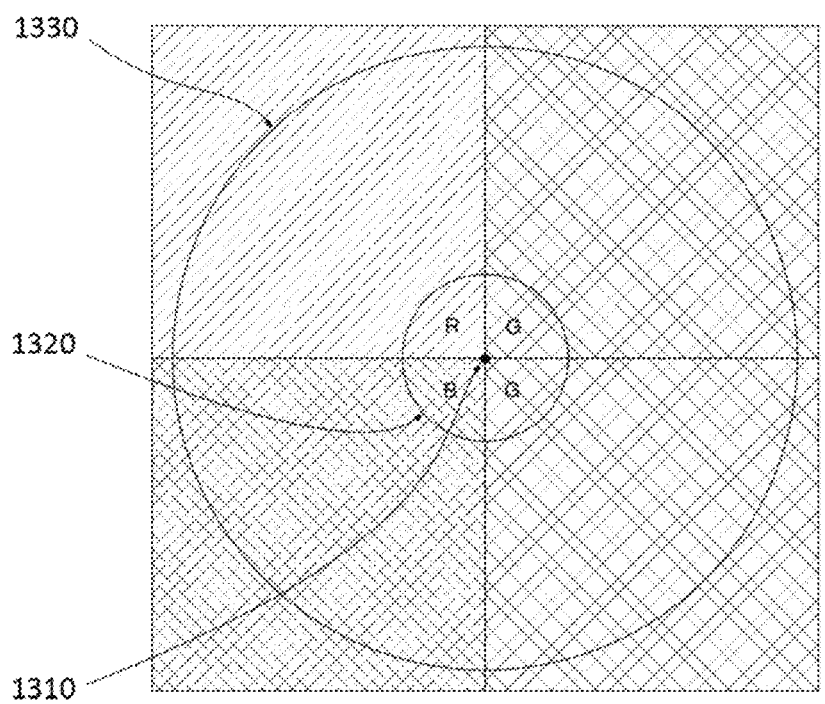
FIG. 13 illustrates a detail view of a bee-eye imager pixel according to an embodiment.

FIG. 13 illustrates a detail view of a bee-eye imager pixel area 1300, according to an embodiment.

The pixel area 1300 may receive light focused by a lens in a lens assembly and transmitted by a corresponding light pipe 1330. The pixel area 1300 may have a larger area than the diameter of the corresponding light pipe 1330. For example, the light pipe 1330 may have a diameter of approximately 7.5 micrometers, and the pixel area 1300 may have an area of 8 micrometers by 8 micrometers.

The pixel area 1300 may be divided into multiple sections, e.g., four sections. Each section may correspond to a light-sensitive photocell. Each of the sections of the pixel area 1300 may correspond to a specific color dye. For example, each section may correspond to one of a red dye, a blue dye, and a green dye. In an embodiment, the sections correspond to a Bayer filter array.

A light-sensitive photocell area 1320 may be located at a center 1310 of the pixel area 1300. The photocell area 1320 may be smaller than the pixel area 1300. For example, the pixel area 1300 may have an area of 8 micrometers by 8 micrometers, and the photocell area 1320 may be circular with a diameter between 0.5 micrometers and micrometers. The resolution of the corresponding imager may increase as the diameter of the photocell area 1320 decreases. The photocell area 1320 may overlap each of the sections of the pixel area 1300. In an embodiment, light passing through the photocell area 1320 is measured by one or more photocells corresponding to one or more photosensors, such as photoresistors, photodiodes, and/or phototransistors.

Light from the light pipe 1330 that falls outside of photocell area 1320 may be rejected by the pixel area 1300. The pixel area 1300 may register light that shines on the photocell area 1320.

Figure 14:
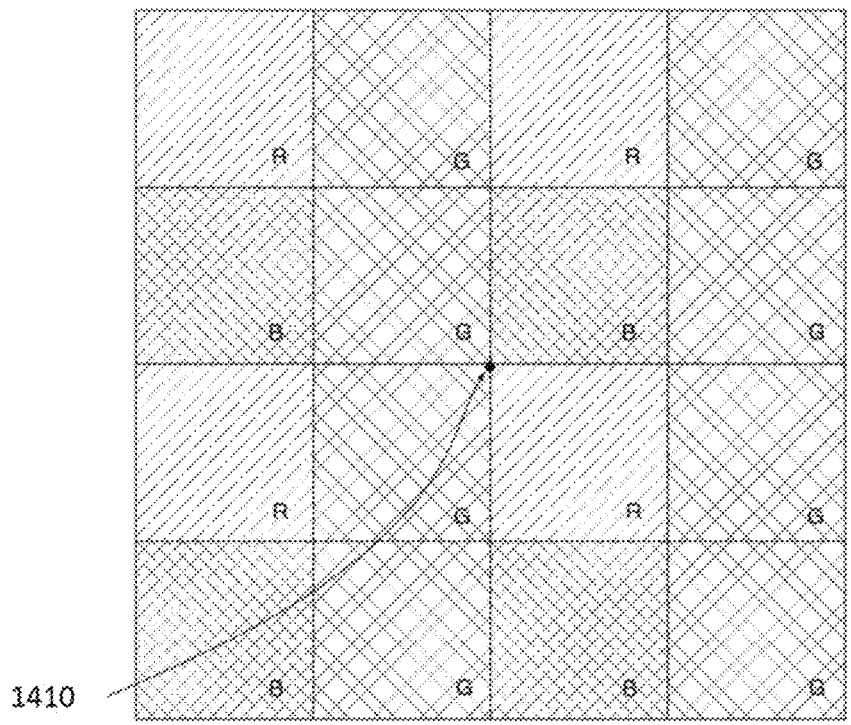
FIG. 14 illustrates a detail view of a bee-eye imager pixel according to an embodiment.

FIG. 14 illustrates a pixel area 1400 with a center 1410. The pixel area 1400 may be divided into 16 sections, each corresponding to a specific color dye. The pixel area 1400 may include four photocell areas, each corresponding to groups of four of the 16 sections. Accordingly, the pixel area 1400 may contain four pixels. In an embodiment, each section may be 2 micrometers by 2 micrometers. The pixel area 1400 may register light that falls onto any photocell area, so that there are no wasted light gathering areas. Accordingly, the pixel area 1400 may achieve maximum light sensitivity.

Figure 15:
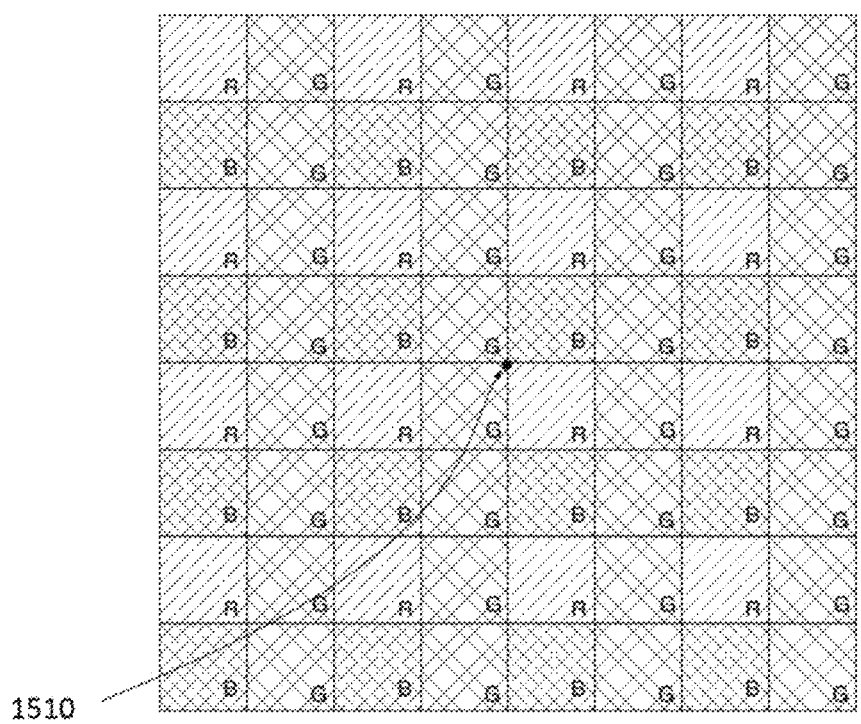
FIG. 15 illustrates a detail view of a bee-eye imager pixel according to an embodiment.

FIG. 15 illustrates a pixel area 1500 with a center 1510. The pixel area 1500 may be divided into 64 sections, each corresponding to a specific color dye. The pixel area 1500 may include 16 photocell areas, each corresponding to groups of four of the 64 sections, such that the pixel area 1500 may contain 16 pixels. In an embodiment, each section may be 1 micrometer by 1 micrometer.

Figure 16:
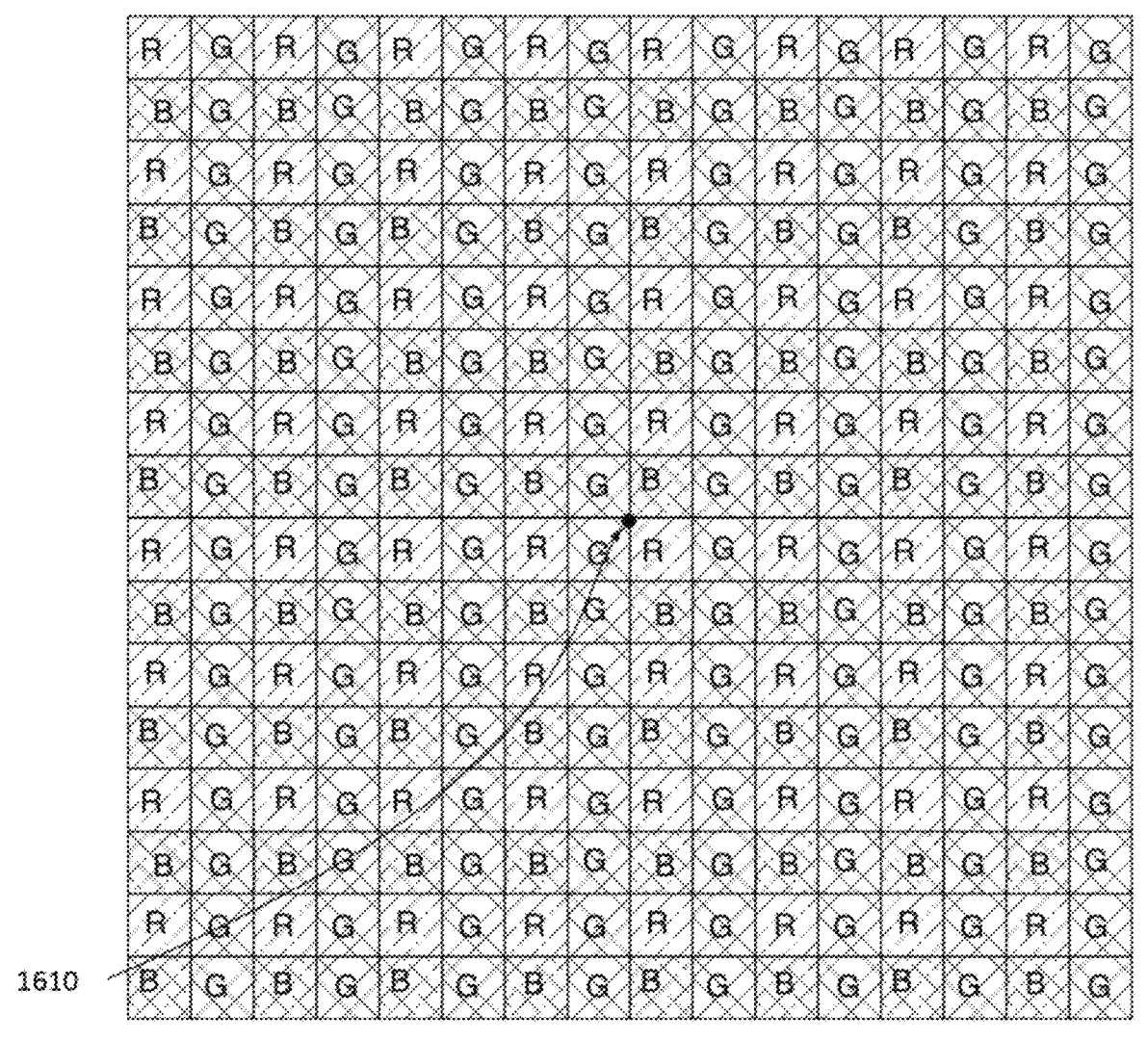

FIG. 16 illustrates a pixel area 1600 with a center 1610. The pixel area 1600 may be divided into 256 sections, each corresponding to a specific color dye. The pixel area 1500 may include 64 photocell areas, each corresponding to groups of four of the 256 sections, such that the pixel area 1600 may contain 64 pixels. In an embodiment, each section may be 0.25 micrometers by 0.25 micrometers.

Figure 17:
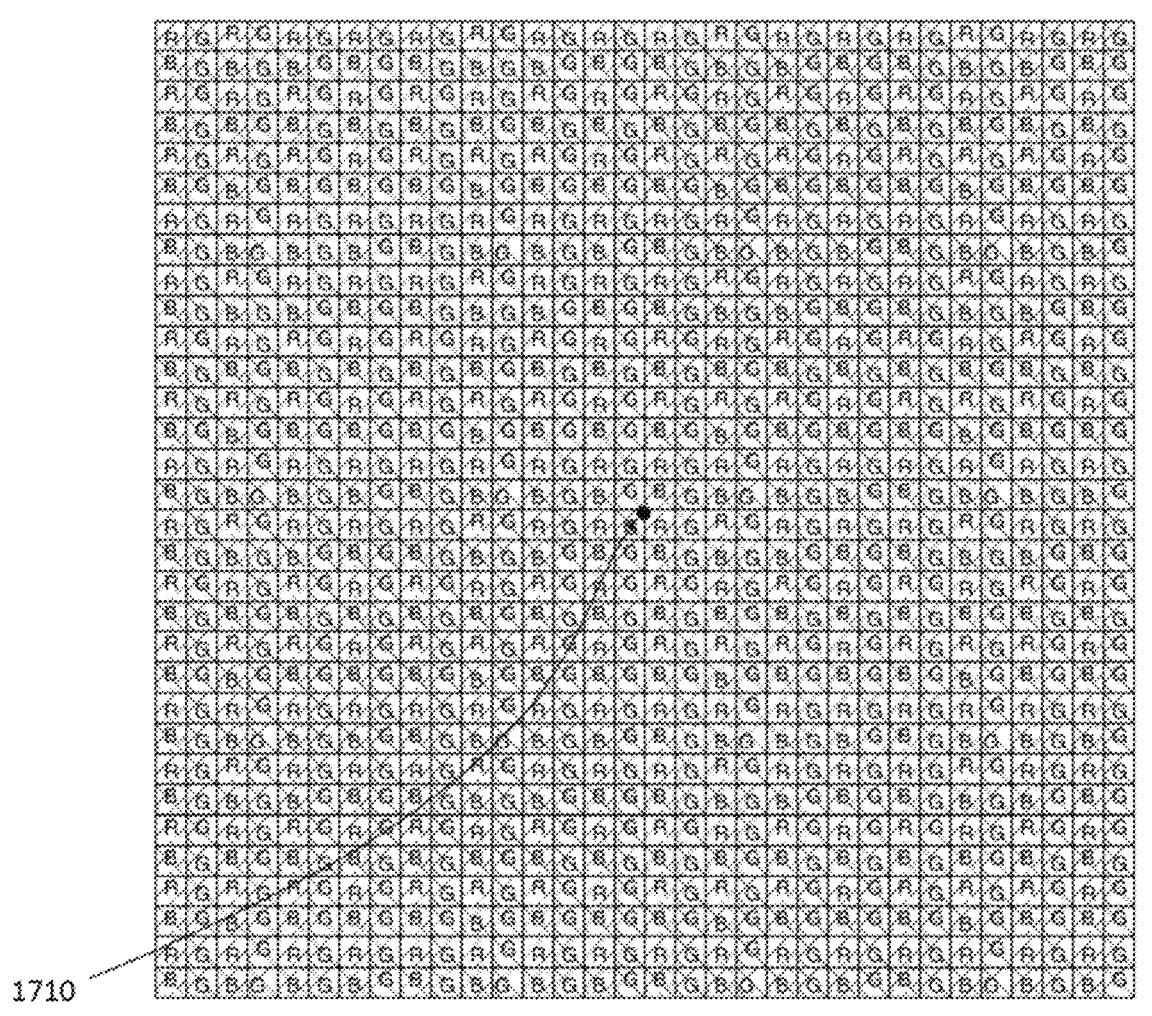

FIG. 17 illustrates a pixel area 1700 with a center 1710. The pixel area 1700 may be divided into 1024 sections, each corresponding to a specific color dye. The pixel area 1700 may include 256 photocell areas, each corresponding to groups of four of the 1024 sections, such that the pixel area 1700 may contain 256 pixels. In an embodiment, each section may be 0.0625 micrometers by 0.625 micrometers.

Figure 18:
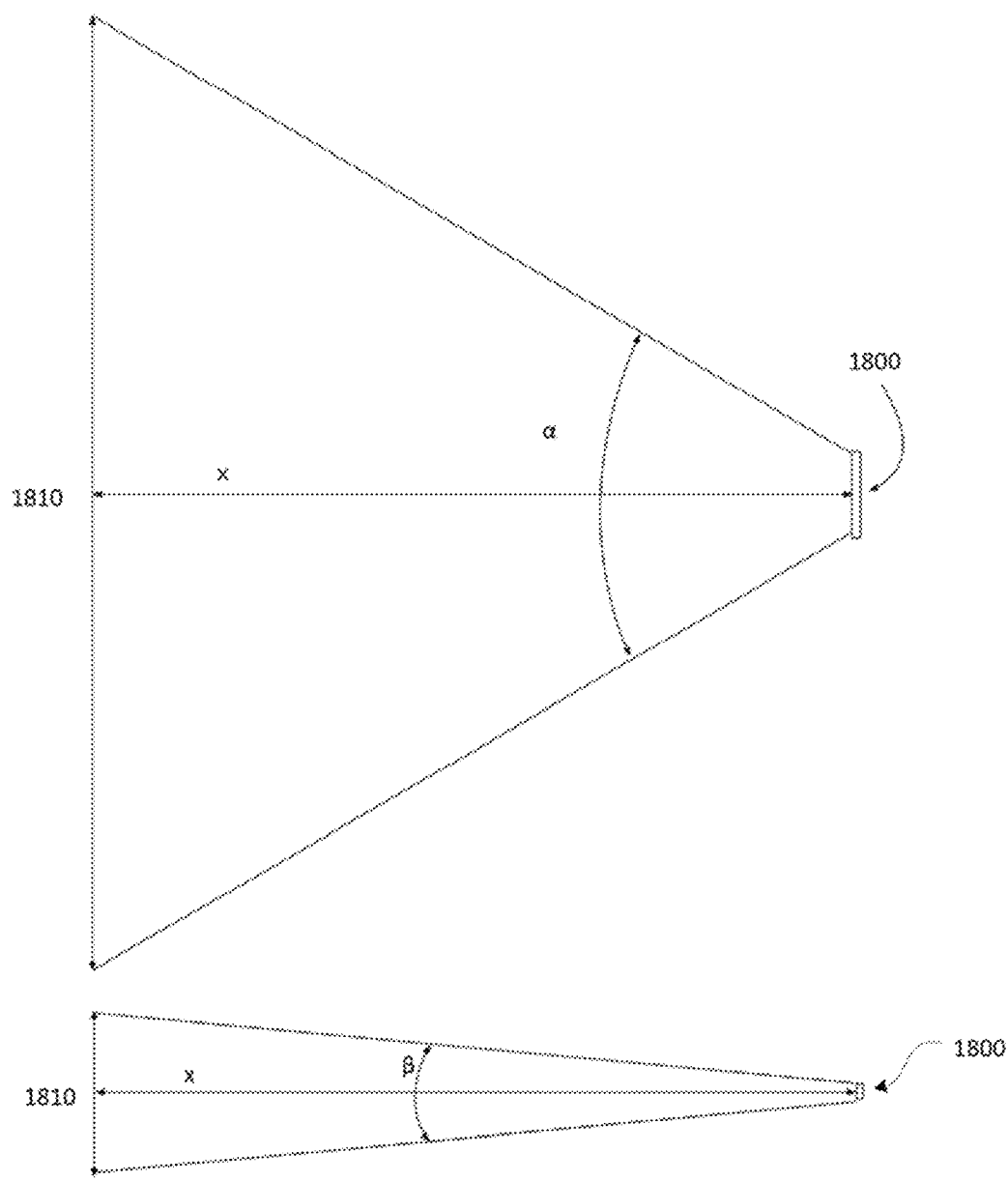
FIG. 18 illustrates horizontal and vertical fields of view of a bee-eye imager according to an embodiment.

FIG. 18 illustrates horizontal and vertical fields of view of a bee-eye imager, according to an embodiment.

The bee-eye imager may have a vertical field of view corresponding to a first angle, and a horizontal field of view corresponding to a second angle.

The first and second angles may be defined with respect to a direction normal to a surface of the bee-eye imager. The bee-eye imager may have a greater vertical length than a horizontal length, and the first angle may be larger than the second angle. In an embodiment, the first angle may be 60 degrees, and the second angle may be 10.56 degrees. The bee-eye imager may have a resolution of multiple pixels per degree. For example, the resolution of the bee-eye imager may be 0.12 degrees per pixel.

FIG. 18 illustrates field of view 1810 of a bee-eye imager 1800, according to an embodiment. The bee-eye imager 1800 may sense light that enters the bee-eye imager 1800 on a rectangular surface. The field of view 1810 may also be rectangular.

The field of view 1810 may be defined by a first angle α along a first axis of the bee-eye imager 1800, and may be defined by a second angle β along a second axis of the bee-eye imager 1800. The first angle α may be greater than the second angle β, such that the field of view 1810 along the first axis is greater than the field of view 1810 along the second axis. In an embodiment, the first angle α is about 120 degrees, and the second angle β is about 21.21 degrees.

Each pixel in the bee-eye imager 1800 may have the same angular field of view along the first axis and the second axis. For example, each pixel may have a field of view of 0.12 degrees along each of the first axis and the second axis. However, the bee eye imager 1800 may include fewer pixels along the second axis than the first axis, which may cause the second angle β to be smaller than the first angle α. For example, the bee-eye imager 1800 may have 500 pixels along the first axis and 88 pixels along the second axis.

The bee eye imager 1800 may have a specific focal distance x. In an embodiment, the focal distance x may be about 35 mm, such that the bee eye imager 1800 can view 44 mm along the first axis and 7.7 mm along the second axis.

Figure 19:
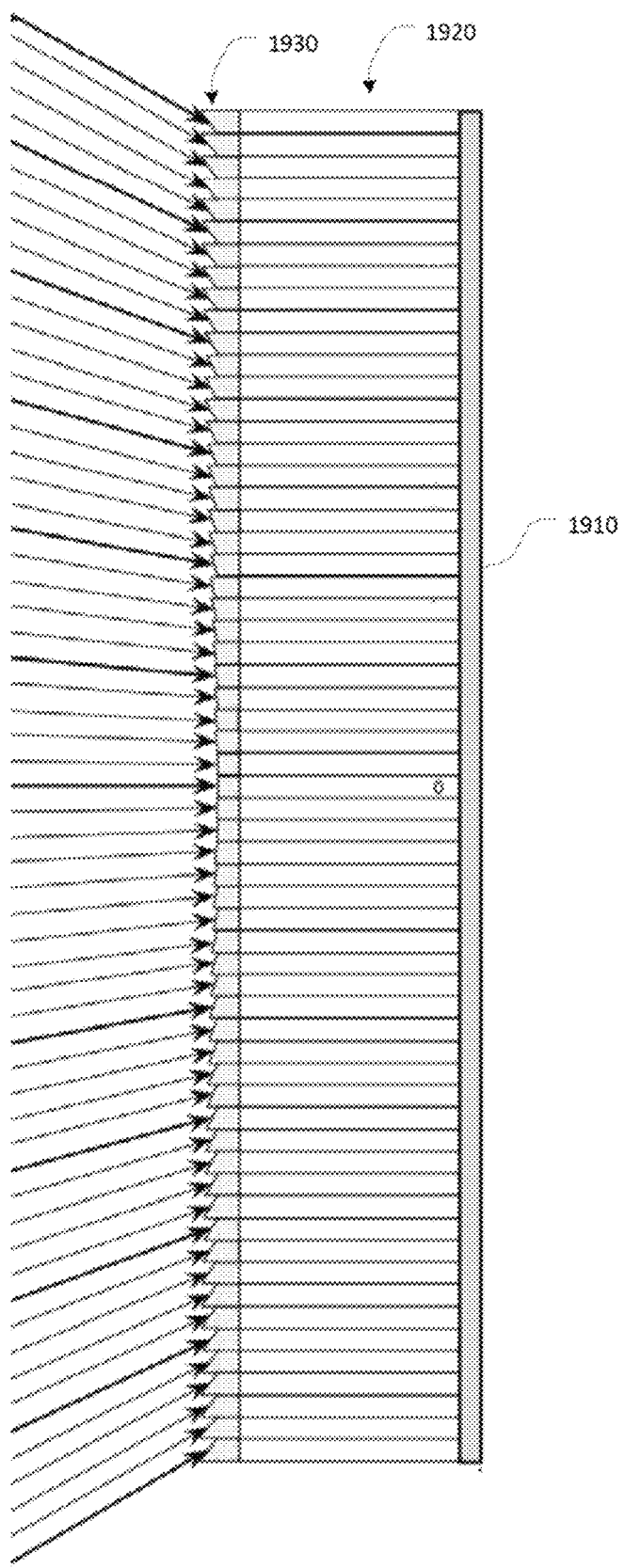
FIG. 19 illustrates a linear pixel array of a bee eye imager, according to an embodiment.

FIG. 19 illustrates a linear pixel array of a bee eye imager, according to an embodiment. In an embodiment, the linear pixel array may include a plurality of pixels arranged in a line with a specific viewing angle. For example, the linear pixel array may have 60 pixels arranged in a line with a total viewing angle of 60 degrees.

The linear pixel array may include an imager chip 1910, a light pipe assembly 1920, and a lens assembly 1930. The imager chip 1910 may include a plurality of photocells optically coupled to a plurality of light pipes in the light pipe assembly 1920. The light pipe assembly 1920 may transmit light from the lens assembly 1930 to the imager chip 1910.

The lens assembly 1930 may include a plurality of lenses that each bend light at a specific angle before transmitting the light to the light pipe assembly 1920. The individual lenses may be faceted, in a similar way to a Fresnel lens. Each lens may direct and focus a portion of the image to an individual pixel photocell in the imager chip 1910. Each faceted lens focuses its respective image through a light pipe in the light pipe assembly 1920. The lens assembly 1930 may be globally concave, but each of the lenses may be individually convex.

Lenses at the outer edge of the lens assembly 1930 may bend light at a greater angle than lenses at the center of the lens assembly 1930. In an embodiment, a lens at the center of the lens assembly 1930 transmits incident light without bending the light beam, whereas a lens at the outer edge of the lens assembly 1930 may bend incident light by 60 degrees before transmitting the light to the light pipe assembly 1920.

Each of the plurality of lenses may have a predetermined angular field of view. For example, each of the plurality of lenses may have a 1 degree field of view. FIG. 19 can be extended into and out of the page and create a 1 degree cone in the third dimension, i.e., a 1 degree steradian.

The resolution of the linear pixel array maybe proportional to a length of the light pipes in the light pipe assembly 1920. For example, the resolution is proportional to the length of the light pipe after the faceted lens and is approximately 0.5 degree for a 100 micrometer light pipe (~ focus length) with a corresponding 2 micrometer diameter photocell.

The depth of focus of the imager chip 1910 may be effectively infinite. For example, the imager chip 1910 may focus on structures that are greater than 10 focal distances from the lenses in the lens assembly 1930.

In an embodiment, imager chip 1910 may have a size of 4 mm by 0.7 mm, a depth of focus that is greater than 1 mm, and the perceived viewed image increases to a field of 10× (or 11× including itself) to a 44 mm by 7.7 mm field of view at a focal distance of 40 mm.

Figure 20:
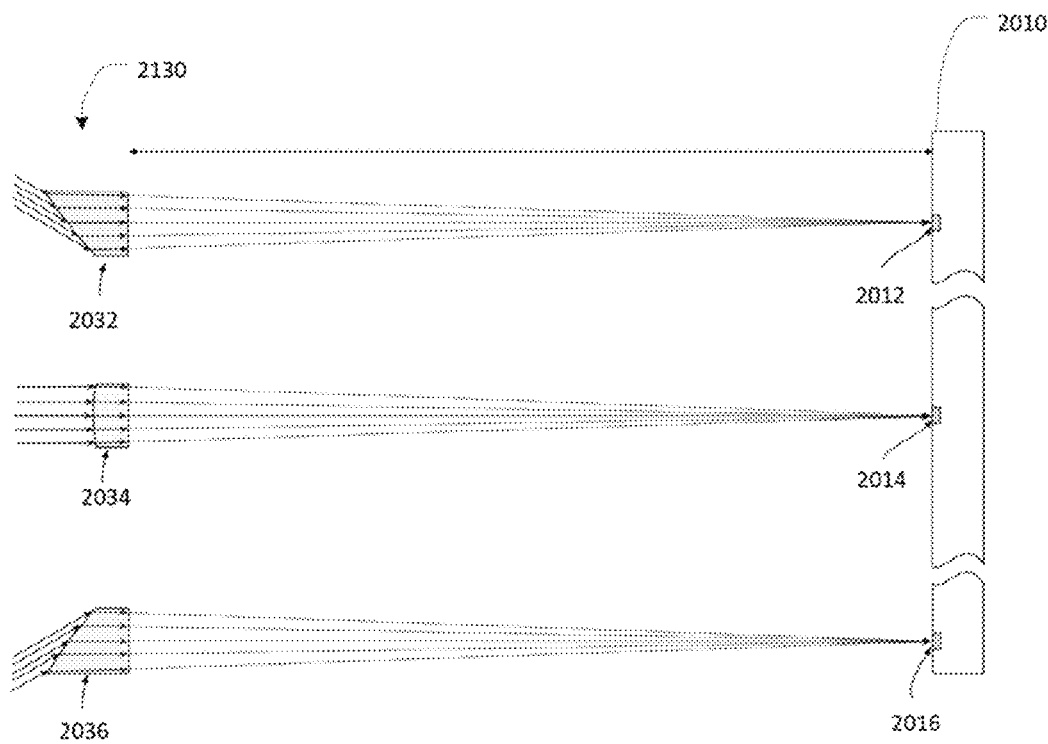
FIG. 20 illustrates one-dimensional pixel photocell targets of a bee-eye imager according to an embodiment.

FIG. 20 illustrates a light diagram of a bee eye imager, according to an embodiment. Specifically, FIG. 20 depicts a light diagram of an imager 2010 and a lens assembly 2030.

The imager 2010 includes a plurality of photocells corresponding to respective light pipes. The plurality of photocells may include a first photocell 2012, a second photocell 2014, and a third photocell 2016. Each photocell may include a photosensor, such as any of a photoresistor, a photodiode, and a phototransistor. In an embodiment, each photocell is 0.5 to 2 micrometers by 0.5 to 2 micrometers, and/or has a diameter of 0.5 to 2 micrometers.

The lens assembly 2030 may include a plurality of lenses, such as a first lens 2032, a second lens 2034, and a third lens 2036. Each of the lenses 2032, 2034, and 2036 may focus light on a respective photocell 2012, 2014, and 2016 through a respective light pipe (not shown). The depth of field may be greater than 10 focal lengths of each of the lenses 2032, 2034, and 2036. Accordingly, the bee eye imager can be used to image objects that are over 10 focal lengths away from the lens assembly 2030.

The lenses 2032, 2034, and 2036 may receive incident light at an angle. Lenses located toward an outer edge of the lens assembly 2030 may receive incident light at a greater angle than lenses located toward a center axis of the lens assembly 2030. For example, the first lens 2032 may accept light at a 330 degree angle, the second lens 2034 may accept light at a 0 degree angle, and the third lens 2036 may accept light at a 30 degree angle.

The lenses 2032, 2034, and 2036 in the lens assembly 2030 may have the same focal length. For example, the focal length may be 100 micrometers.

The position of respective lenses and photocells can be described on an x-axis. In an embodiment, the first lens 2032 has a position of x=250, the second lens 2034 has a position of x=0, and the third lens 2036 has a position of x=−250. Similarly, the first photocell 2012 may have a position of x=250, the second lens 2014 may have a position of x=0, and the third photocell may have a position of x=−250. The angle at which a lens accepts light may be proportional to the x position of the lens.

Figure 21:
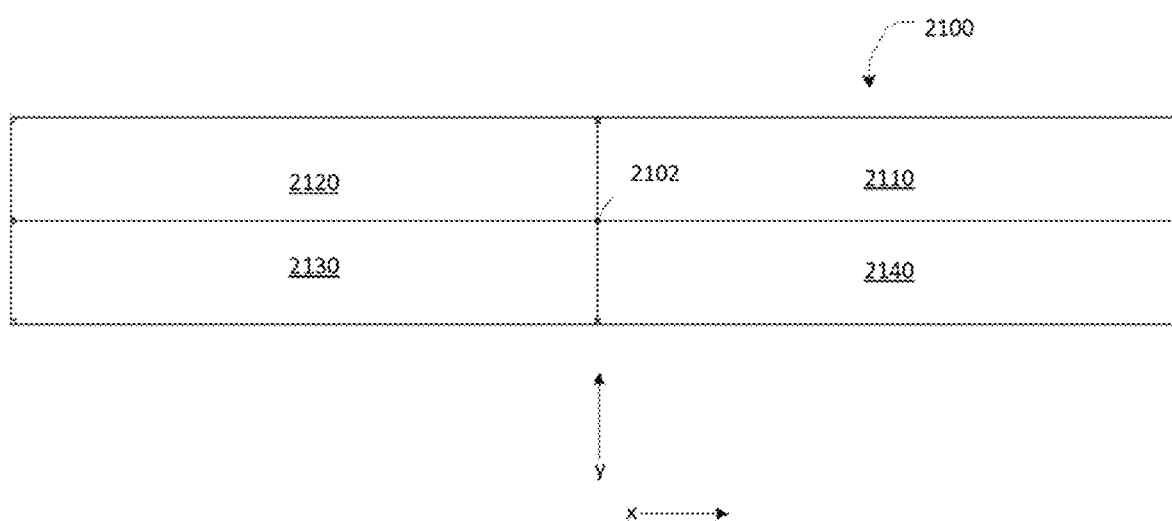
FIG. 21 illustrates pixel positioning nomenclature according to an embodiment.

FIG. 21 illustrates pixel positioning nomenclature of a bee eye imager 2100, according to an embodiment.

The bee eye imager 2100 may include a plurality of pixels arranged in a rectangular grid along an x direction and a y direction. Each pixel may have a respective position in the rectangular grid defined by x and y. For a pixel at the center of the bee eye imager, x may be 0 and y may be 0. For a pixel in a first quadrant 2110 of the bee eye imager, x and y may be positive integers. For a pixel in a second quadrant 2120, x may be a negative integer and y may be a positive integer. For a pixel in a third quadrant 2130, x and y may be negative integers. For a pixel in a fourth quadrant 2140, x may be a positive integer and y may be a negative integer. In an embodiment, x may range from [−250, 250], and y may range from [−44, 44], such that the bee eye imager 2100 may have a length of 500 pixels and a height of 88 pixels.

Figure 22:
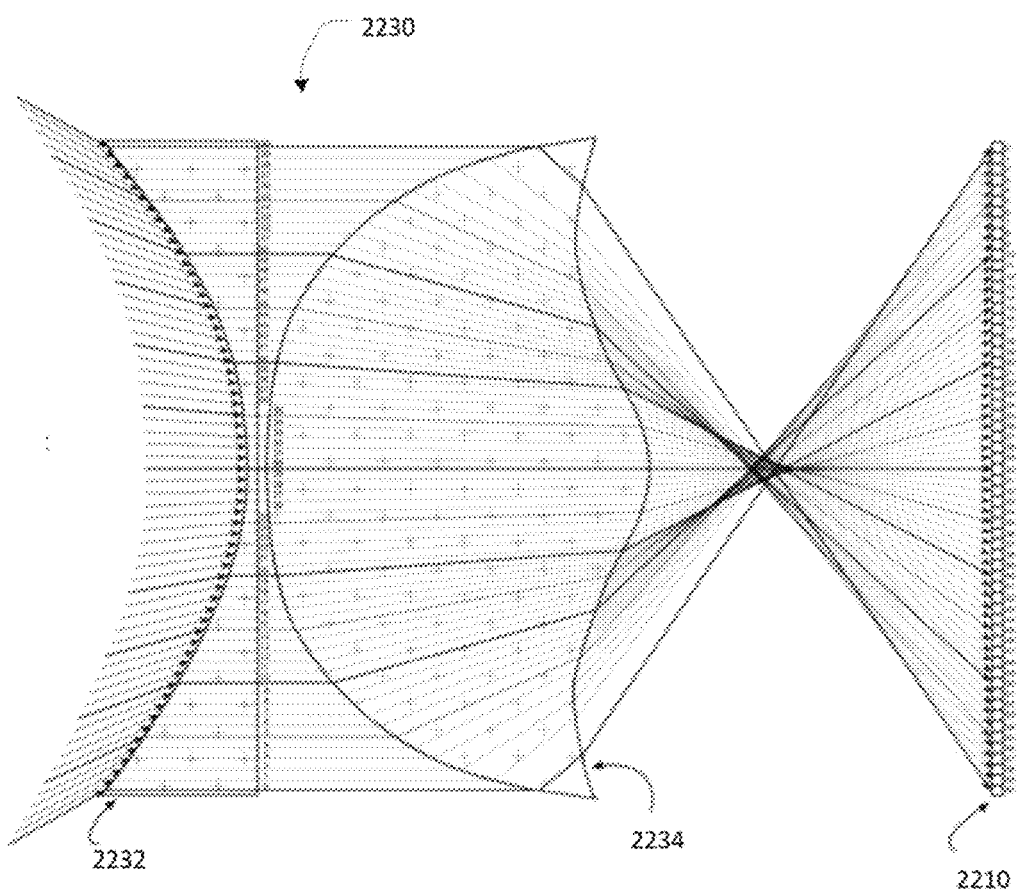
FIG. 22 illustrates an imager and a lens assembly according to an embodiment.

FIG. 22 illustrates an imager 2210 and a lens assembly 2230, according to an embodiment.

The lens assembly 2230 may include first and second continuous lenses 2232 and 2234. The first continuous lens 2232 may be a concave lens, which may convert light from a 60 degree field of view to parallel light rays. The second lens 2234 may be a concave lens that may focus the parallel light rays to pixels on the imager.

The lens assembly 2230 of FIG. 22 may have a greater thickness than the lens assembly 1930 and light pipe assembly 1920 of FIG. 19, for example, but may utilize the same design rules. For example, the lens assembly 2230 may have a thickness of 830 micrometers, and the lens assembly 1930 and light pipe assembly 1920 of FIG. 19 may have a collective thickness of 120 micrometers using similar design rules. In some applications, the thinner lens assembly 1930 and 1920 may be preferred over the lens assembly 2230.

Figure 23:
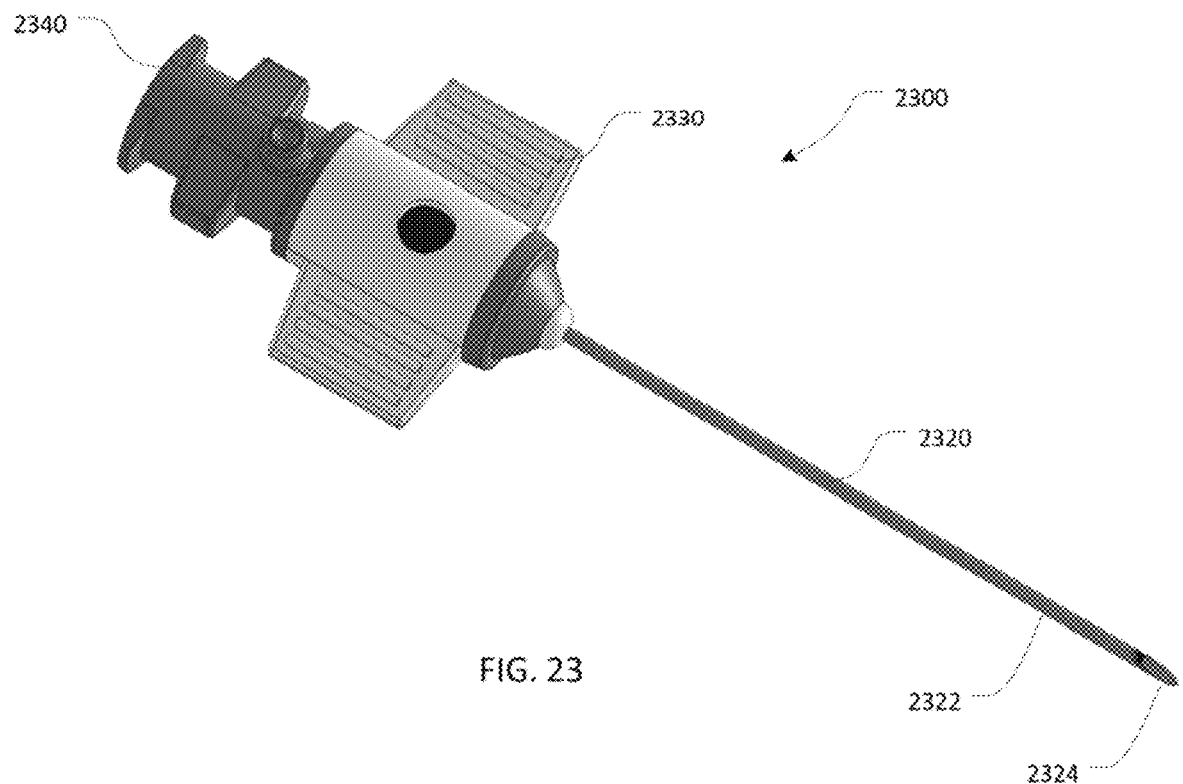
FIG. 23 illustrates an imaging needle apparatus when a probe tip is hidden within a needle according to an embodiment of the disclosure.
Figure 24:
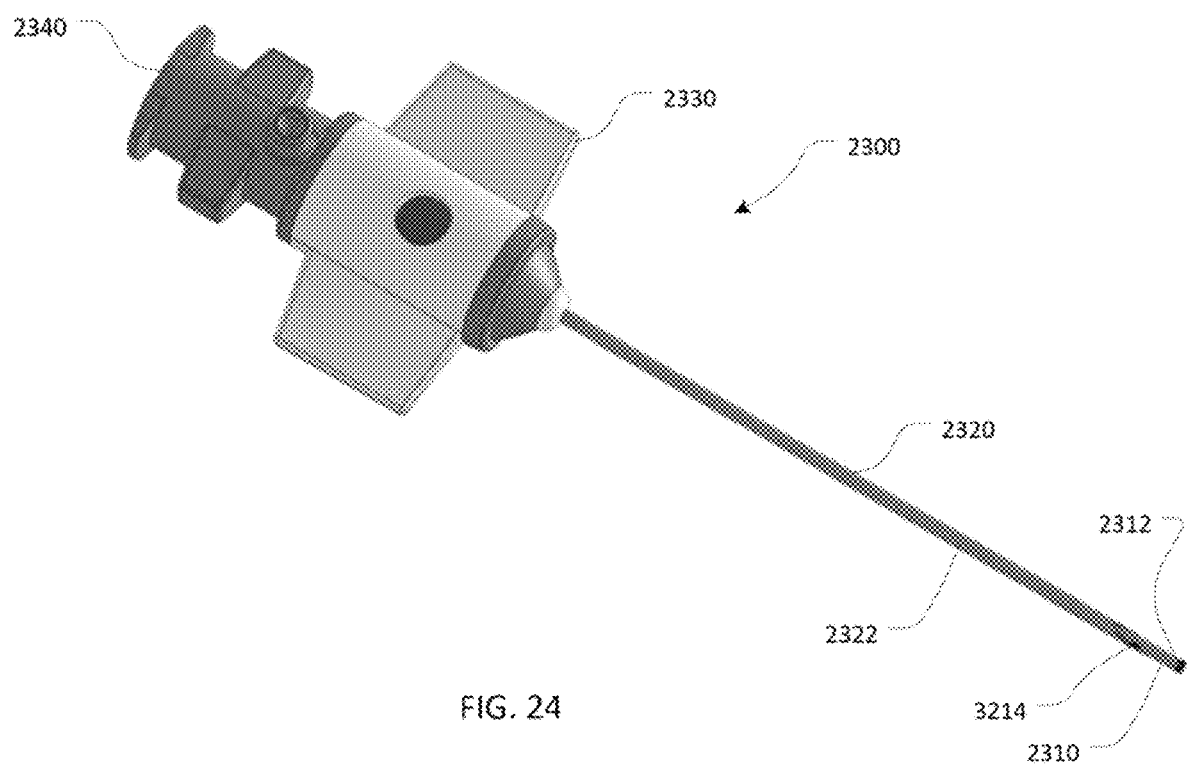
FIG. 24 illustrates an imaging needle apparatus when a probe tip is exposed according to an embodiment of the disclosure.

FIG. 23 illustrates an imaging needle apparatus when a probe tip provided within a needle according to an embodiment of the disclosure. FIG. 24 illustrates the imaging needle apparatus of FIG. 23 when the probe tip is exposed according to an embodiment of the disclosure. The imaging needle apparatus may be used to image a site, as well as to inject materials into the site.

In an embodiment, an imaging needle apparatus 2300 includes a needle 2320, a body 2340 (e.g., a syringe), and a probe 2310. The needle 2320 includes a needle body or tube 2322 (e.g., metallic tube having a circular cross-section) and a sharp tip 2324. The probe 2310 includes a tip 2312 having a blunt front end.

In an embodiment, the needle 2320 houses the probe 2310, where the probe 2310 may be housed within the needle 2320 (see FIG. 23) or exposed (see FIG. 24) from the needle according to the modes of operation for the imaging needle apparatus. is In an embodiment, the probe 2310 may be extended or retracted relative to the needle 2310 based on an operation being performed. For example, the imaging needle apparatus may retract the probe 2310 into the needle 2320 to use the sharp tip 2324 of the needle to pierce tissues as needed. Materials may be injected through the needle. The materials may be fluid, therapeutic materials, such as injectable drugs and/or cell suspensions. In an embodiment, the materials may be injected through a side hole 2314 in the tip of the probe.

The body 2340 (e.g., a syringe) may store the materials that can be injected through the needle, and may be used to exert pressure on the materials so that the materials are driven through the needle. The body 2340 may include an output port used to connect imaging circuitry in the imaging needle apparatus to an external device, e.g., a device including a display screen. In the present embodiment, the body 2340 is a syringe that is capable of storing liquid, and the term "syringe" hereinafter is used to referred to "body." However, the term "body" alone is not limited to the term "syringe."

The body 2340 may include one or more fins 2330. The fins 2330 may be turned by a user around an axis parallel to the needle 2320. The probe of the needle 2320 may be selectively retracted by turning the fins 2330. For example, FIG. 23 illustrates the fins 2330 in a position corresponding to a retracted state of the probe, and FIG. 24 illustrates the fins 2330 in a position corresponding to an extended state of the probe.

The fins 2330 may further include an indicator displaying whether the probe is extended or retracted. For example, the indicator may be circular and may be colored based on whether the probe is extended or retracted. In an embodiment, the indicator may be green when the probe is extended, and may be red when the probe is retracted. Because the indicator is located on the body 2340, rather than the needle 2320, a user can use the indicator to confirm whether the probe is retracted when the needle 2320 is injected into an opaque material.

Figure 25:
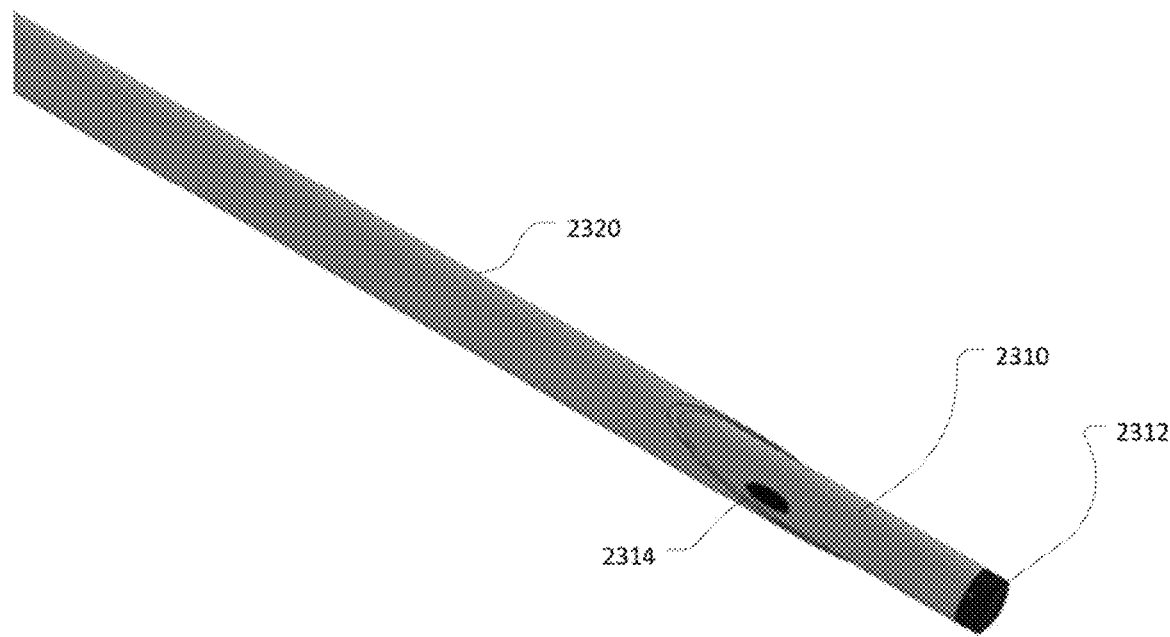
FIG. 25 illustrates a tip of a imaging needle apparatus according to an embodiment of the disclosure.

FIG. 25 illustrates a tip of a needle 2320 according to an embodiment of the disclosure. Specifically, FIG. 25 illustrates a probe 2310 extending from the tip of the needle 2320. As illustrated, the probe 2310 is surrounded by a needle.

An imaging apparatus may be disposed inside of the probe 2310, and may image spaces pointing in an axial direction from the tip of the tip of the probe 2310. That is, the imaging apparatus may point through the tip of the probe 2310, which may be covered.

Materials injected through the needle 2320 may be injected from the probe 2310. Specifically, the materials may be injected through one or more side ports on an outer circumferential surface of probe 2310. When the probe 2310 is extended, the side ports of the probe 2310 may be exposed. Accordingly, the materials may be injected into a space simultaneously while imaging the space.

Figure 26A:
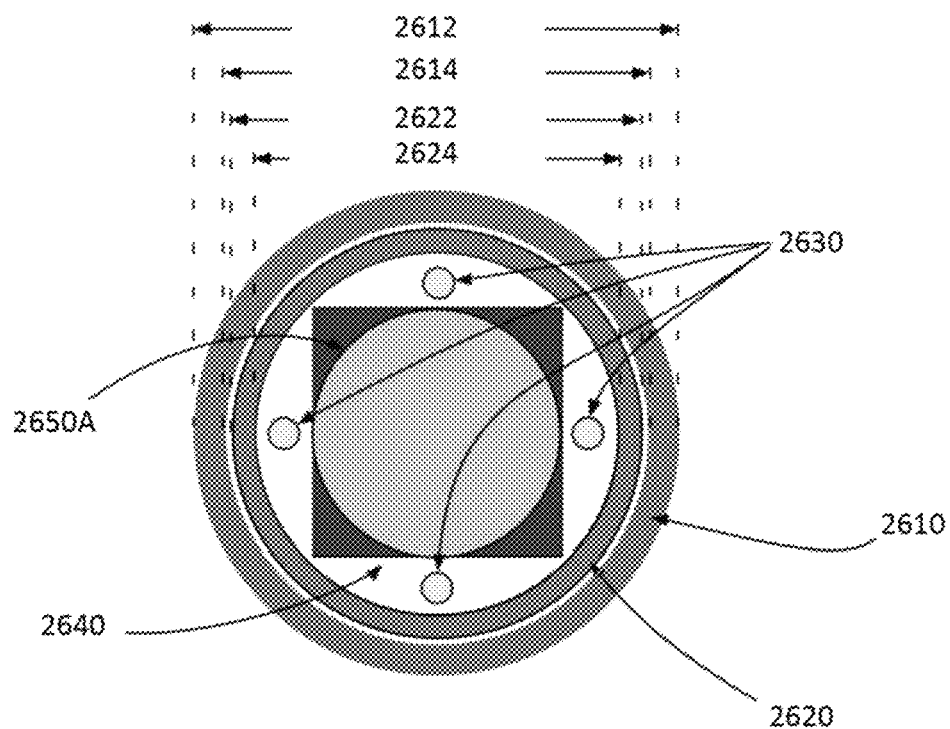
FIG. 26A illustrates a cross section of a needle syringe, and an imager assembly in a probe tip of the needle syringe, from a tip view according to an embodiment of the disclosure.
Figure 26B:
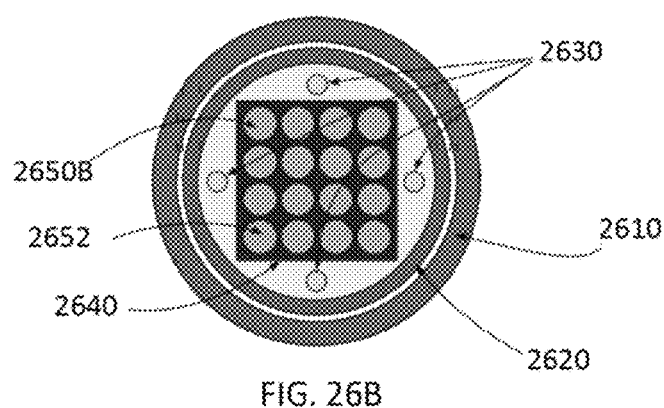
FIG. 26B illustrates a cross section needle syringe, and an imager assembly in a probe tip of the needle syringe, from a tip view according to an embodiment of the disclosure.

FIGS. 26A and 26B illustrate cross sections of imaging needle apparatuses from a tip view according to an embodiment of the disclosure.

The imaging needle apparatus of FIG. 26A may include an outer cover 2610, an inner cover 2620, a plurality of light pipes 2630, an imager 2640, and a lens 2650A. The imaging needle apparatus may further include a cover (not illustrated) covering the tip of the imaging needle apparatus.

The outer cover 2610 may have a circular cross-section. In an embodiment, the outer cover 2610 may correspond to a 21 gauge needle, with an outer diameter 2612 of 819 microns, and with an inner diameter 2614 of 700 microns.

The inner cover 2620 may have a circular cross-section. In an embodiment, the inner cover 2620 may correspond to a 22.5 gauge needle, with an outer diameter 2622 of 667 microns and an inner diameter 2624 of 579 microns.

The plurality of light pipes 2630 may be disposed between an inner wall of the inner cover 2620 and the imager 2640. The plurality of light pipes 2630 may extend down the length of the imaging needle apparatus. The plurality of light pipes 2630 may emit light from the tip of the imaging needle apparatus, which may illuminate a target area that can be imaged by the imager 2640. In an embodiment, the plurality of light pipes 2630 may be coupled to one or more LEDs. In an embodiment, each of the plurality of light pipes 2630 may have a diameter of 50 microns.

The imager 2640 may be disposed inside of the inner cover 2620 and may be covered by the lens 2650A. The imager 2640 may have a different shape than the inner surface of the inner cover 2620. In an embodiment, the imager has a square, 400 micron by 400 micron cross-section. The imager 2640 may include circuitry and a plurality of photocells that generate imaging signals.

The lens 2650A may focus light onto the imager 2640. The lens 2650A may be a single, cylindrical structure. In an embodiment, the lens 2650A may have a different cross-sectional shape than the imager 2640.

The imaging needle apparatus of FIG. 26B is similar to the imaging needle apparatus of FIG. 26A. However, the imaging needle apparatus of FIG. 26B includes a lens assembly 2650B in place of the lens 2650A. The lens assembly 2650B may include a plurality of individual lenses 2652 that respectively focus light onto the imager 2640. In an embodiment, each of the plurality of lenses 2652 may focus light on one of the photocells of the imager 2640. The lens assembly 2650B may be a Fresnel lens, and the lens assembly 2650B and the imager 2640 may be part of a bee-eye imager.

In an embodiment, each of the plurality of lenses 2652 may have a diameter of 85 microns.

Figure 27:
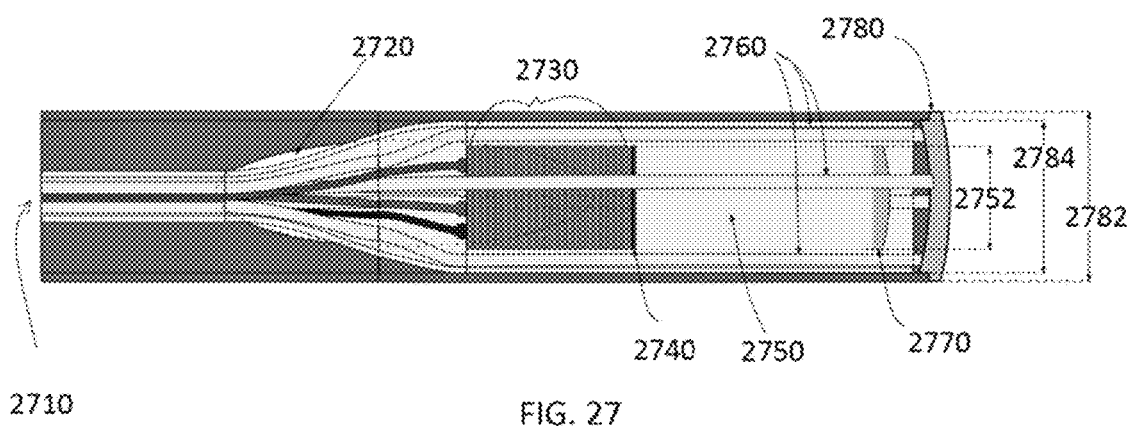
FIG. 27 illustrates a diagram of an imager assembly in a probe tip according to an embodiment of the disclosure.
Figure 28:
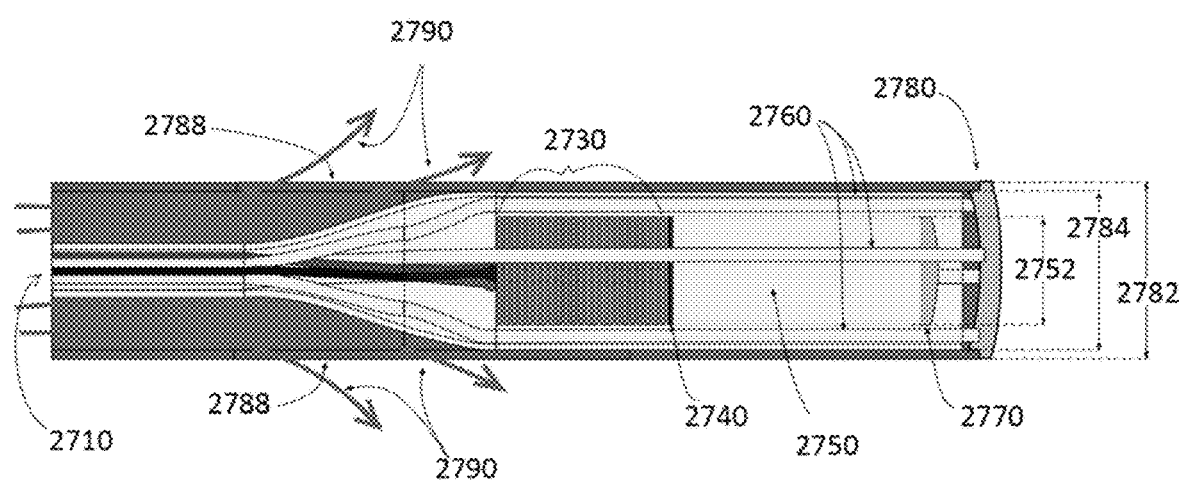
FIG. 28 illustrates a diagram of an imager assembly in a probe tip and fluid flow through the imager lens assembly according to an embodiment of the disclosure.

FIG. 27 illustrates a probe of an imaging needle apparatus according to an embodiment of the disclosure. FIG. 28 illustrates the probe of FIG. 27 emitting fluid according to an embodiment of the disclosure.

The probe includes a bundle 2710, a side port opening 2720, a stack 2730, an imager chip 2740, a focusing light pipe 2750, a plurality of illumination light pipes 2760, a lens 2770, and a cover 2780.

The bundle 2710 may include a plurality of cables and the plurality of illumination light pipes 2760. The plurality of cables may be micro USB cables. In an embodiment, each of the cables may include a 25 micron gold or silver core with a 2.5 micron layer of insulation around the gold or silver core. The bundle 2710 may extend from the stack 2730. The bundle 2710 may transmit light through the illumination light pipes 2760 and transmit imaging signals from the stack 2730.

The side port opening 2720 may be a hole in the cover 2780. Materials may be injected to a target space through the side port opening 2720. For example, a fluid 2790 may be injected through the side port opening 2720.

The stack 2730 may produce imaging signals based on electrical signals produced by the imager chip 2740. The stack 2730 may include a plurality of ICs. The stack 2370 and the imager chip 2730 may be part of an imager, for example, a bee-eye imager.

The imager chip 2740 may receive light and produce electrical signals based on the received light. The imager chip 2740 may be stacked on the stack 2730, and may be electrically coupled to the stack 2730. The imager chip 2740 may be disposed between the stack 2730 and the focusing light pipe 2750. The imager chip 2740 may include a plurality of photocells, corresponding to a plurality of pixels.

The focusing light pipe 2750 may channel light from the lens 2770 to the imager chip 2740.

The plurality of illumination light pipes 2760 may be used to transmit light from the probe to an external area to be imaged. The plurality of illumination light pipes 2760 may extend from the bundle 2710, and along outer walls of the stack 2730, the imager chip 2740, and the lens 2770. The plurality of illumination light pipes 2760 may be fiber optic cables.

The lens 2770 may focus light received by the probe to the imager chip 2740.

The cover 2780 may be disposed around the probe. The cover 2780 may emit materials through the side port, which may be located between a body and the stack 2730. Accordingly, the fluid 2790 may not flow between the cover 2780 and the stack 2730, the imager chip 2740, the focusing light pipe 2750, and the lens 2770. The cover 2770 may have a sidewall 2788 and a transparent cap. Light from the plurality of illumination light pipes 2760, and light to the lens 2770, may flow through the transparent cap.

In an embodiment, the cover 2780 may have an outer diameter of 0.667 mm, an inner diameter of 0.592 mm, and the lens 2770 may have a diameter of 0.400 mm.

Figure 29:
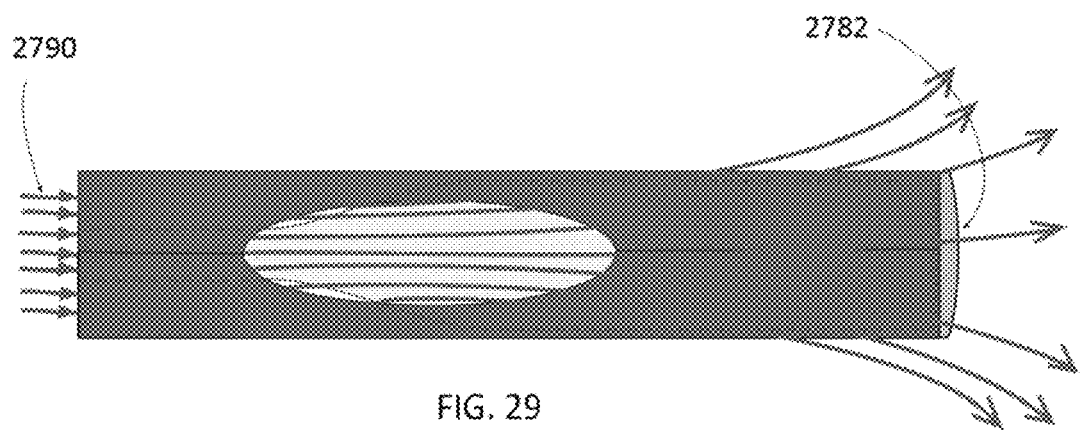
FIG. 29 illustrates a fluid flow diagram of a syringe according to an embodiment of the disclosure.

FIG. 29 illustrates a fluid flow diagram of probe according to an embodiment of the disclosure. Fluid 2790 may be injected through a needle and through a side port in a cover 2782 of the probe.

Figure 30:
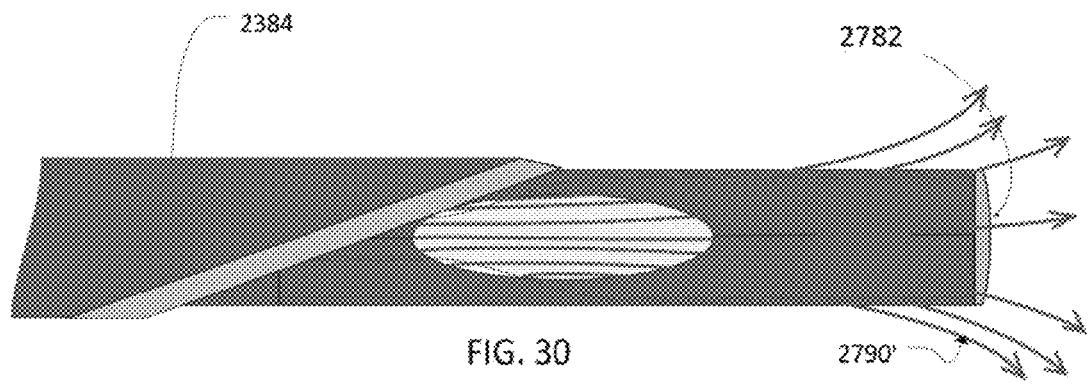
FIG. 30 illustrates a side view of a tip of a needle syringe including a probe tip and a covered cutting edge according to an embodiment of the disclosure.

FIG. 30 illustrates fluid flow diagram of a probe and a needle according to an embodiment of the disclosure. When the probe is extended, a side port in a cover 2782 of the probe may be uncovered. Accordingly, fluid 2790' may flow from the side port without being inhibited by the needle 2384.

Figure 31A:
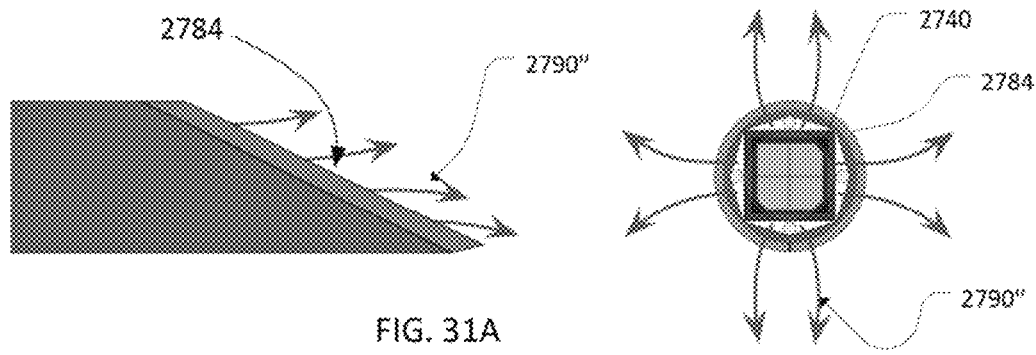
FIGS. 31A and 31B show views of fluid flow through a needle syringe having a retractable tip, according to an embodiment.
Figure 31B:
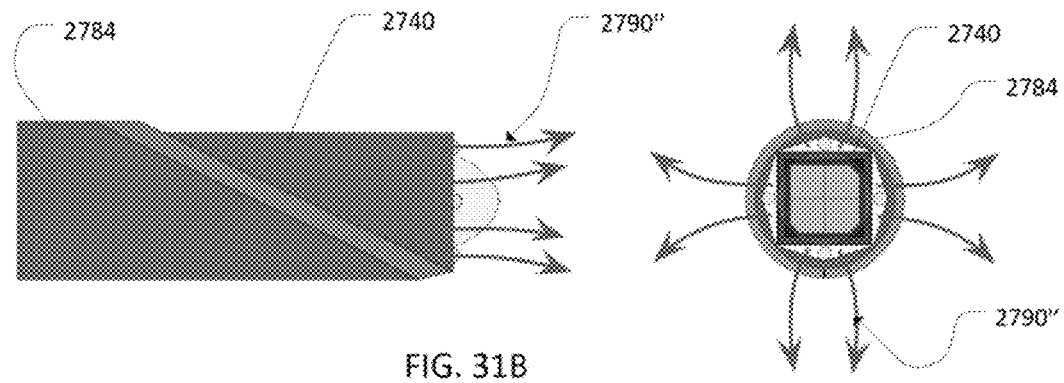

FIGS. 31A and 31B show side and tip views of fluid flow through an imaging needle apparatus having a retractable probe, according to an embodiment. FIG. 31A shows fluid flow through the imaging needle apparatus when the probe 2740 is fully retracted. FIG. 31B shows fluid flow through the imaging needle apparatus when the probe 2740 is partially retracted.

The probe 2740 of the imaging needle apparatus may be surrounded by a needle 2782, which may extend beyond the tip of the probe 2740 when the probe 2740 is retracted.

Fluid 2790" may be emitted from the needle through the probe 2740 when the probe 2740 is fully or partially retracted. During imaging, the fluid 2790" may flow through lumens at the tip of the probe 2740. The lumens may be disposed in the cover of the probe 2740, and may be between illumination light pipes in the probe 2740. The fluid through the lumens may be used to clear the viewing field of debris or tissue.

Figure 32:
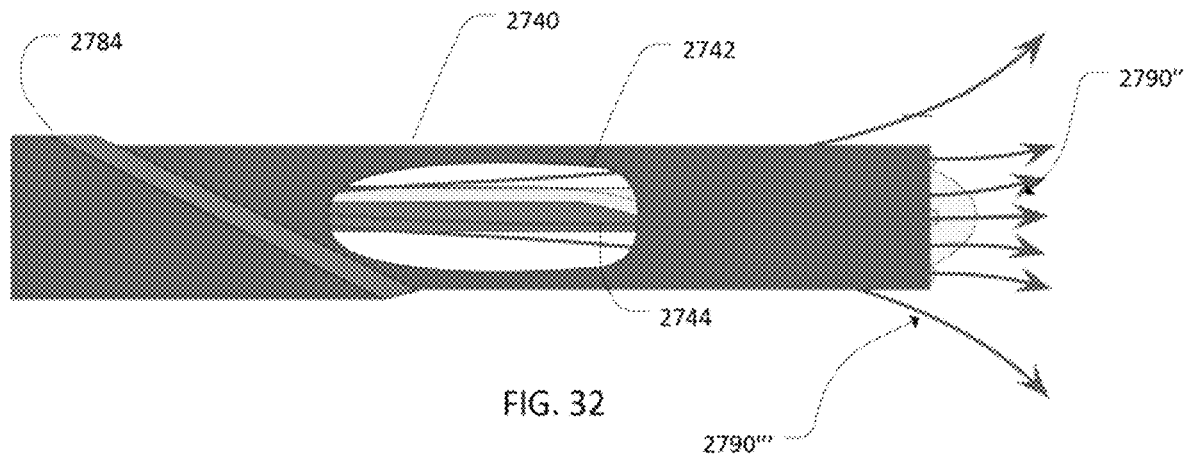
FIG. 32 shows a view of fluid flow through a needle syringe having a retractable tip, according to an embodiment.

FIG. 32 shows a side view of fluid flow through an imaging needle apparatus having a retractable probe, according to an embodiment. FIG. 32 shows fluid flow through the imaging needle apparatus when a probe 2740 extends from a needle 2784. An imager inside of the probe 2740 may be connected with an external device via a bundle 2744. The bundle 2744 may include a plurality of cables and a plurality of light pipes. Fluid 2790''' may flow through one or more side ports 2742 in the probe 2740. The one or more side ports 2742 may be adjacent to the bundle 2744.

Figure 33:
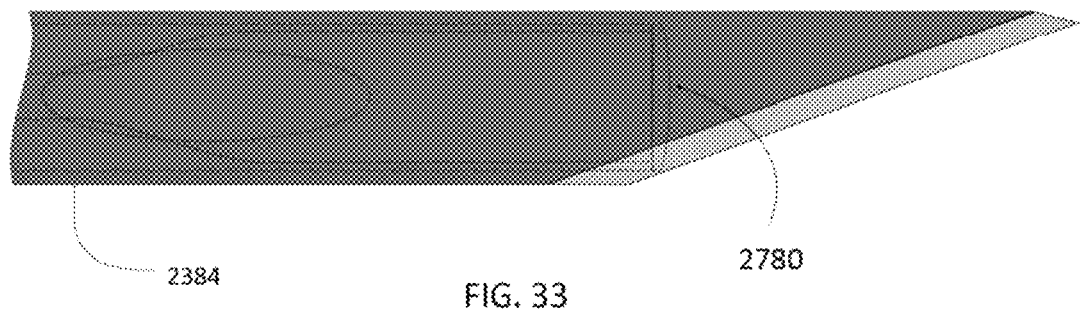
FIG. 33 illustrates a side view of a probe tip with an exposed cutting edge according to an embodiment of the disclosure.

FIG. 33 illustrates a side view an imaging needle apparatus having an exposed cutting edge according to an embodiment of the disclosure. The imaging needle apparatus may include a probe 2780 and a needle 2384. The probe 2780 may be retracted with respect to the cover 2384. Accordingly, the needle may extend from the tip of the imaging needle apparatus.

Figure 34:
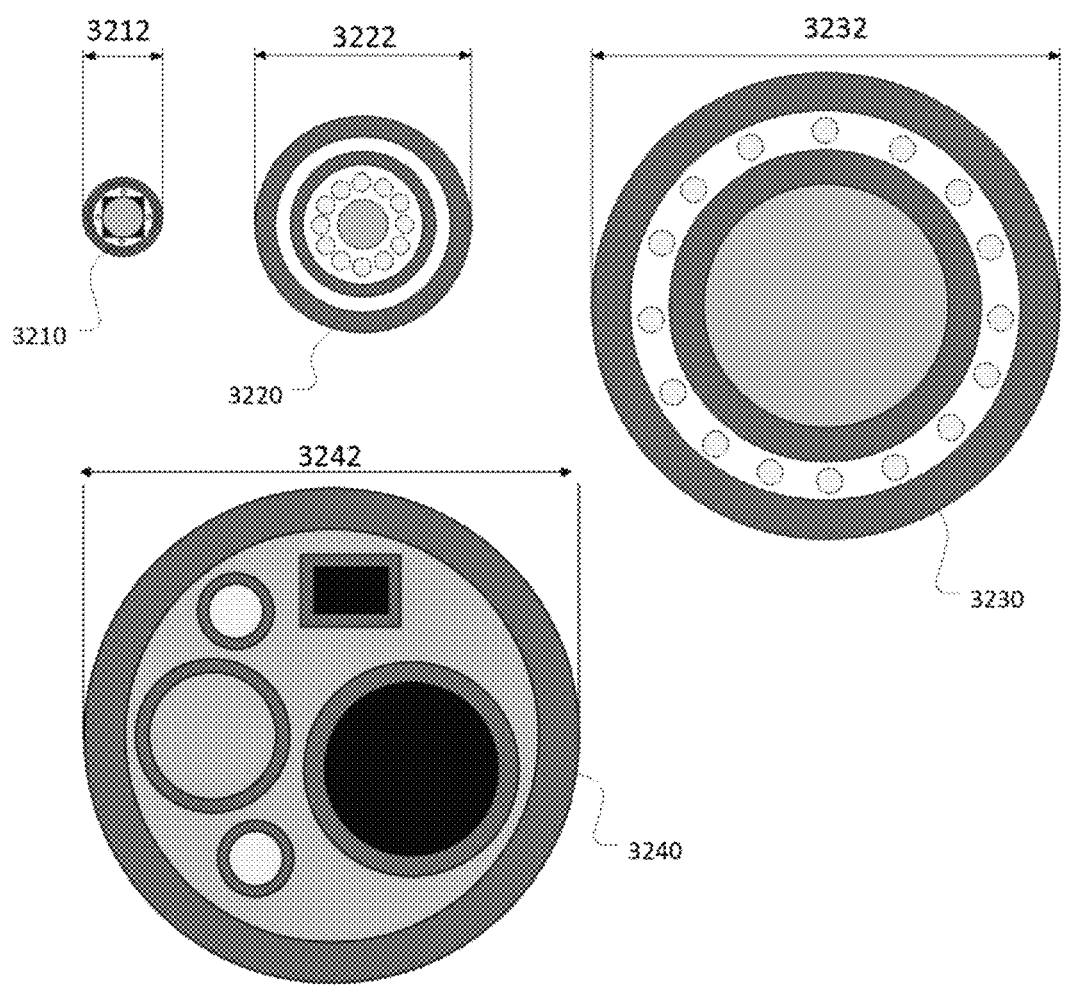
FIG. 34 illustrates cross sections of the imaging needle apparatus and other devices according to an embodiment of the disclosure.

FIG. 34 illustrates cross sections of the imaging needle apparatus and other devices according to an embodiment of the disclosure. Specifically, FIG. 34 illustrates the cross sections of an imaging needle apparatus 3210 according to an embodiment, a minimally invasive imager 3220, and first and second standard arthroscopes 3230 and 3240. The minimally invasive imager 3220 may, for example, be a 14 gauge Mi-Eye™ by Trice Medical. The first and second arthroscopes may each be 7 gauge standard arthroscopes. In an embodiment, the imaging needle apparatus may have a diameter of 0.82 mm, the minimally invasive imager 3220 may have a diameter of 2.11 mm, and each of the first and second arthroscopes 3230 and 3240 may have a diameter of 4.57 mm.

The imaging needle apparatus 3210 has a relatively small cross-section compared to the minimally invasive imager 3220 and the first and second standard arthroscopes 3230 and 3240. The minimally invasive imager 3220 may have a cross-sectional area that is 6.6 times the size of the cross-sectional area of the imaging needle apparatus 3210. The first and second standard arthroscopes 3230 and 3240 may have cross-sectional areas that are 32.1 times the size of the cross-sectional area of the imaging needle apparatus 3210. Accordingly, the imaging needle apparatus 3210 according to an embodiment may have a relatively small puncture area compared to other devices.

Figure 35:
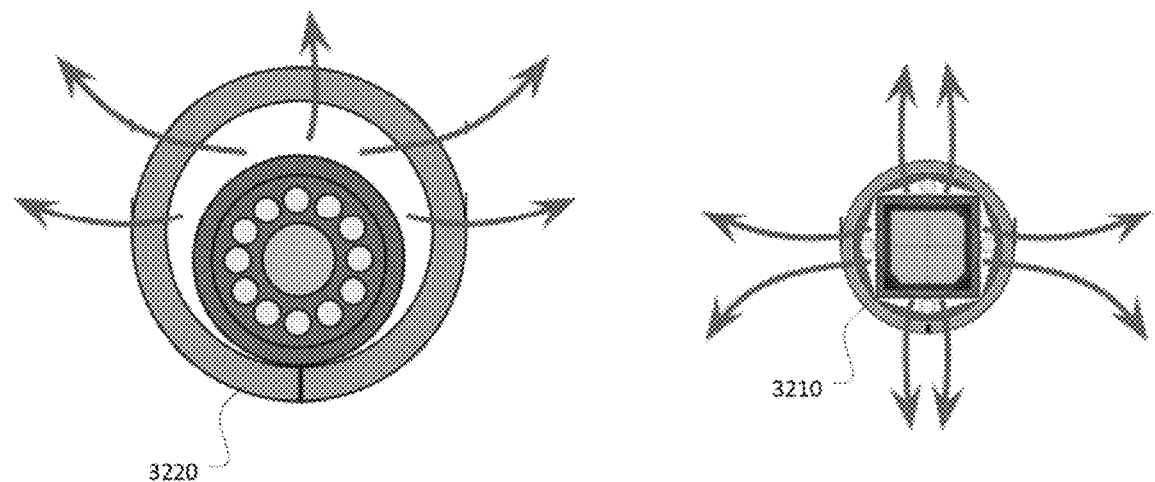
FIG. 35 illustrates fluid flowing from a tip of the imaging needle apparatus and from the tip of another device according to an embodiment of the disclosure.

FIG. 35 illustrates fluid flowing from a tip of an imaging needle apparatus according to an embodiment and from the tip of another device. Fluid flow from the imaging needle apparatus 3210 may be symmetrically distributed around an inner probe. In contrast, fluid flow through a needle of the other device, e.g., a minimally invasive imager 3220, may be unevenly distributed around an imaging device inside of the needle.

The minimally invasive imager 3220 uses substantially smaller diameter inner needle to act as an opening or as a lumen to allow fluid flow between the inner and outer needles to clear its viewing field. However, this spacing does not allow full shielding of the sharp outer cutting edge and may cause unintentional nicking, cutting, or other collateral injury to the surrounding tissue. As such, the sharp outer cutting edge is not fully covered. In contrast, a probe and an outer needle of the imaging needle apparatus 3210 have similar diameters, and thus the needle can be fully covered when the probe is extended.

Figure 36:
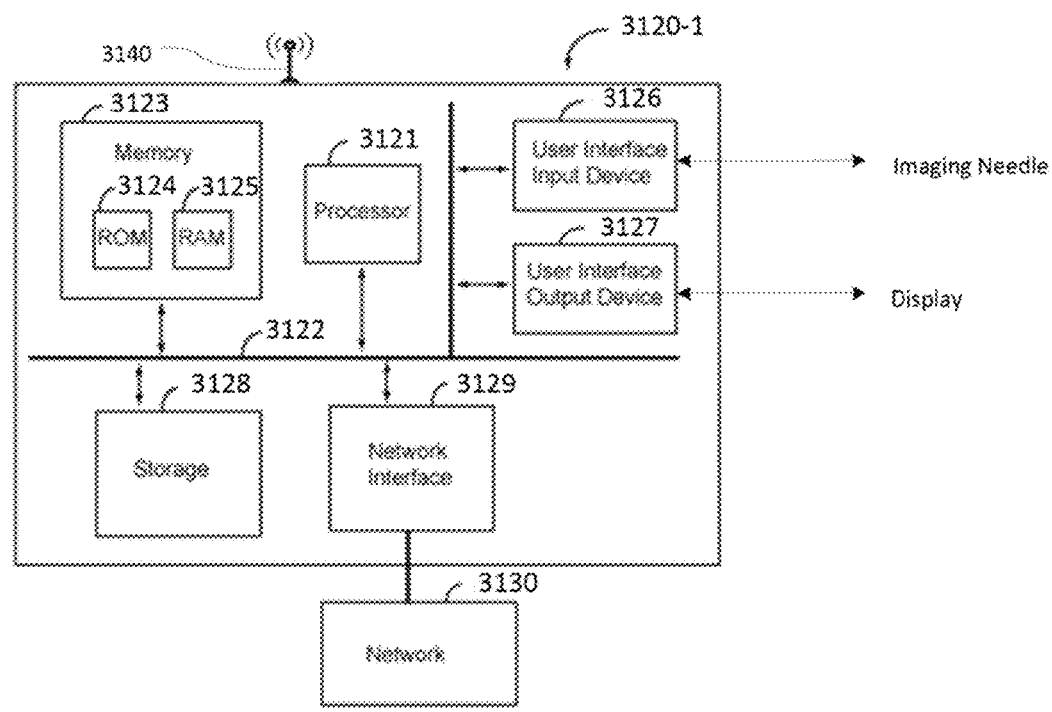
FIG. 36 illustrates a computer system according to an embodiment of the disclosure.

FIG. 36 illustrates a computer system according to an embodiment of the disclosure.

A computer system 3120-1 may include one or more of a processor 3121, a memory 3123, a user input device 3126, a user output device 3127, and a storage 3128, each of which communicates through a bus 3122. The computer system 3120-1 may also include a network interface 3129 that is coupled to a network 3130. The processor 3121 may be a central processing unit (CPU) or a semiconductor device that executes processing instructions stored in the memory 3123 and/or the storage 3128. The memory 3123 and the storage 3128 may include various forms of volatile or non-volatile storage media. For example, the memory may include a read-only memory (ROM) 3124 and a random access memory (RAM) 3125.

Accordingly, an embodiment of the invention may be implemented as a computer implemented method or as a non-transitory computer readable medium with computer executable instructions stored thereon. In an embodiment, when executed by the processor, the computer readable instructions may perform a method according to at least one aspect of the invention.

In an embodiment, the user interface output device 3127 may be coupled to a display. The display may be configured to display images and/or videos output through the bus 3122.

The user interface input device 3126 may be coupled to an imaging needle apparatus, via a wired or wireless connection. The user interface input device 3126 may receive image signals from the imaging needle apparatus, corresponding to images captured by an imager assembly of the imaging needle apparatus. The processor 3121 may convert the image signals into a format suitable for output to the display. For example, the processor 3121 may filter the image signals. In an embodiment, the processor 3121 may be integrated into an IC stack within a probe of the imaging needle apparatus.

The computer system 3120-1 may further include a wireless transceiver 3140. The wireless transceiver 3140 may transmit signals from the bus 3122 to an external device, and/or receive signals from an external device. For example, the wireless transceiver 3140 may transmit imaging signals to the display, and/or may receive imaging signals from the imaging needle apparatus.

The imaging needle apparatus may be used as an arthroscope. Due to the small size of the imager in the imaging needle syringe, no positive pressure apparatus may be necessary to perform an arthroscopic procedure, unlike traditional arthroscopes. A user can use the imaging needle apparatus in an office setting, in order to provide a variety of injections.

The imaging needle apparatus may include a 21.5 G needle. The cutting edge of the needle may be covered or uncovered.

The video lens may be located on the tip of the imaging needle apparatus. The imaging needle apparatus may therefore be suitable for recording forward-viewing imaging and/or video recording through the lens. The lens may be extendable when, for example, the fins are twisted. The fins may be twisted along a direction circumferential to the needle. The lens may be locked in place, and the cutting edge of the needle may be covered when the video lens is extended.

The video lens allows users to easily navigate the tip of the needle into human joints and other spaces. When the video lens is inside a joint or space, the probe may be extended and the cutting edge of the needle may be actively covered or uncovered during a procedure.

A tip of the probe may be coated so that it can be easily located using ultrasound. The coating on the tip may also provide additional guidance during use.

The imager assembly may include a bee-eye imager, according to an embodiment of the present disclosure.

Once in place, the needle may be used for more precise targeting of fluids into imaged spaces. A retractable probe in the needle may include ports that can deliver injections of stem cells, platelet-rich plasma (PRP), biological glues or other materials with precision.

The imaging needle apparatus can be operated in various ways. For example, a user could place the tip into a patient's joint using the extended needle, image the joint using the imaging assembly, identify a meniscal tear or flap in the joint based on the imaged joint, and treat the meniscal tear or flap. The user may treat the meniscal tear or flap by gluing the tear or flap down, shave off at least a portion of the meniscal tear or flap, and/or inject stem cells/PRP through the needle into the joint, as the case dictates. The whole procedure may be easily recorded (e.g., by video) using the imaging assembly for documentation or future reference. Alternatively, the imaging needle apparatus can be used to image spaces in order to guide a second micro needle tool that can cut or otherwise manipulate tissues as needed.

The imaging according to embodiments of the present disclosure may be much smaller and even less invasive (i.e., more suited for minimally invasive procedures) than traditional instruments. In an embodiment, the small imager housed probe can be disposed inside of a relatively small needle, as compared to traditional instruments.

In addition, embodiments of the present disclosure may have many other applications besides orthopedics applications. Embodiments can be readily adapted to all manner of scopes and catheters and will have a wide application to the many fields in medicine. For example, embodiments of the imaging needle apparatus could be used to further miniaturize cardiac catheters, which can allow safer intra-vascular navigation and placement. The imaging needle apparatus may also be used as, or may become, a much smaller laproscope.

In addition, embodiments of the present disclosure could be also used for needle guidance and tissue biopsies of all types. For example, the imaging needle apparatus may be inserted into a tissue, and allow a user to recognize and confirm tissue changes through the lens. Accordingly, the imaging needle apparatus can be used to more accurately biopsy tissue as needed.

The imaging needle apparatus, according to an embodiment, may be used to perform growingly important percutaneous procedures. According to an embodiment, the small size of the needle and forward viewing lens system may be used to assist all manner of office-based diagnostics and procedures.

Eventually, current open surgical procedures performed in a hospital setting may one day be easily and safely done without general anesthesia in an office procedure setting using embodiments of the imaging needle apparatus. Embodiments of the imaging needle apparatus will not only make procedures more convenient for both patients and doctors, but they could also significantly reduce patient risk and health costs.

Embodiments relate to an imaging needle apparatus. The imaging needle apparatus may have a body attached to a needle with a retractable tip. For example, the imaging needle may include a as well as a probe. The may be sufficiently sharp enough to pierce soft tissue, and the probe may be used to image the surrounding environment.

Either one of the and the probe may be retractable. When the probe extends beyond the sharp tip of the needle, the imaging needle may be blunt. When the sharp tip of the needle extends beyond the blunt tip of the probe, the imaging needle may be sharp.

The tolerances between the and the probe are such that only enough spacing is present to assure unimpeded protraction and retraction of the probe with respect to the. Such tight tolerances allow shielding of the outer sharp cutting edge when the probe is protracted.

The retraction operation can be performed via a control mechanism. The probe may be retracted and housed inside of the needle when the control mechanism is in a first state, and may be extended from the sharp tip of the needle when the control mechanism is in a second state. The control mechanism may be provided on the body. The control mechanism may include, for example, fins that extend radially from the body. The control mechanism may include two fins that extend on opposite sides of the body. A user may perform the retraction by rotating the fins. The fins may be rotated around a rotation axis that is parallel to the needle.

The fins may also be accompanied by an indicator that shows whether the imaging needle is in a retracted state. The indicator may be colored, and may display a different color based on whether the imaging needle is retracted. Accordingly, the indicator can inform the user of whether the blunt tip of the probe extends beyond sharp tip of the needle when the retractable tip is not visible to the user.

In an embodiment, the imaging needle may be used solely as an imaging device, or may be used as an imaging device and as a means to deliver fluid into a desired space. Fluid may flow through the needle according to pressure applied by the body of the imaging needle. The fluid may flow out of the needle through holes in the side of the probe when the probe extends beyond the sharp tip of the needle. Fluid may also flow through lumens at the tip of the probe. The lumens may be disposed in the cover of the probe, and may be between illumination light pipes in the probe. The fluid through the lumens may be used to clear the viewing field of debris or tissue. During viewing, all of the fluid flow may occur through the lumens.

The body may exert pressure on the fluid using, for example, a syringe, a bulb, a pump, and/or a similar structure.

An imager in the probe may be used to image the surrounding environment through a transparent cover on the distal end of the probe. A distal end of the probe may be the farthest end of the probe from the body of the imaging needle apparatus. The imager may be disposed distal to the holes in the sides of the probe.

The diameter of the needle may be relatively small, because the imager can be relatively small. The imager may include one or more cables, a stack of ICs, an imager chip, one or more light pipes, and a lens. The imager may be a bee-eye imager apparatus. The imager may include an IC stack comprising a plurality of photocells, and a lens assembly. The lens assembly may include a Fresnel lens.

The one or more cables can transmit electrical signals between a port on the body of the imaging needle apparatus and the rest of the imager. The port on the body of the imaging needle apparatus may be used to connect the imaging needle apparatus to an external device, such as a computer, a display, or both.

The stack of ICs may and the imager may be used to convert light signals into the usable electrical signals transferred through the one or more cables. The imager may correspond to a plurality of pixels. The resolution of the imager corresponds to the number of photocells and/or pixels in the imager.

The one or more light pipes may guide light to and from the cover of the probe. The light pipes may include illumination light pipes, which may transmit light through the cover in order to illuminate an area that is being imaged. The illumination light pipes may be disposed along the interior of the probe. The illumination light pipes may extend along an outer edge of the imager chip and the IC stack, and may be bundled with the one or more cables. The illumination light pipes may guide light from one or more LEDs.

The one or more light pipes may also include a focusing light pipe. The focusing light pipe may be disposed between the imager chip and the lens of the imager. The focusing light pipe may transmit focused light from the lens to the imager. The illumination light pipes may be disposed around an outer circumference of the focusing light pipe.

The lens may be disposed between the imager and the cover of the imaging needle apparatus. The lens may focus light onto the imager.

The cover may be disposed over the probe. The cover may be transparent, such that light from the illumination light pipes may be transmitted through the cover.

In an embodiment, the imaging needle apparatus captures video, includes a 21 gauge needle, has a puncture area of 0.53 mm$^2$, has a pixel size of 1.13 microns by 1.13 microns, has a pixel count of 98,000, and has an active imager chip area of 0.13 mm$^2$.

In an embodiment, the imaging needle apparatus has a 2D lens diameter of 400 microns, a first focal length of 100 microns with a field of view of 120 degrees and a zoom of 0.5×, a second focal length of 200 microns with a field of view of 60 degrees and a zoom of 1×, a third focal length of 400 microns with a field of view of 30 degrees and a zoom of 2×, and a fourth focal length of 800 microns with a field of view of 15 degrees and a zoom of 4×.

In an embodiment, the imaging needle apparatus has a lens array with 16 lenses, each having a diameter of 85 microns, a first focal length of 100 microns with a field of view of 60 degrees and a zoom of 0.5×, and a second focal length of 200 microns and a field of view of 30 degrees and a zoom of 1×.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. An imaging needle apparatus, comprising:
   a body;
   a needle coupled to the body, the needle including a needle body and a sharp tip;

a probe including a blunt tip that can be exposed from the needle or housed within the needle according to an operation being performed with the image needle apparatus, the blunt tip of the probe being retractable from the sharp tip of the needle;

an imager disposed inside of the probe, the imager including a plurality of photocells; and a control mechanism provided on the body, the control mechanism having a first state and a second state, wherein the blunt tip configured to be retracted to be housed within the needle body when the control mechanism is in the first state and extended from the needle and exposed when the control mechanism is in the second state, and wherein the control mechanism includes a plurality of fins extending from the body, the plurality of fins being configured to rotate in a circumferential direction.

2. The apparatus of claim 1, wherein the needle body is hollow, the probe being disposed inside of the needle body.

3. The apparatus of claim 1, wherein the body is configured to exert a pressure in a space inside of the probe.

4. The apparatus of claim 3, wherein the body includes a syringe configured to exert the pressure in the space.

5. The apparatus of claim 3, wherein the probe has a plurality of side ports, the side ports being holes through a side of the probe, and wherein when the body exerts the pressure on fluid inside of the probe space, the fluid is emitted through the side ports.

6. The apparatus of claim 5, wherein the probe has a plurality of lumens, the lumens being holes through the blunt tip of the probe, and wherein when the body exerts the pressure on the fluid inside of the probe space, the fluid is emitted through the lumens.

7. The apparatus of claim 1, further comprising:

a lens assembly disposed inside of the probe, the lens assembly including a plurality of lenses respectively focusing light on the plurality of photocells of the imager, the lens assembly comprising a Fresnel lens; and a plurality of illumination light pipes extending along an outer surface of the imager and an outer surface of the lens assembly, the plurality of illumination light pipes transmitting light through the blunt tip of the probe.

8. The apparatus of claim 1, further comprising:

a bundle disposed inside the probe, the bundle including a cable, wherein the imager includes an imager chip and a stack of integrated circuits (ICs) coupled to the imager chip, the imager chip including the plurality of photocells arrayed in a grid, the stack of ICs processing imaging signals from the photocells of the imager, the cable transmitting the processed imaging signals from the stack of ICs.

9. The apparatus of claim 8, wherein the body includes a port, the port being coupled to the cable.

10. The apparatus of claim 1, wherein the blunt tip of the probe is transparent.

11. A system, comprising:

an imaging needle apparatus including:

a body;

a needle coupled to the body, the needle including a needle body and a sharp tip;

a probe including a blunt tip that can be exposed from the needle or housed within the needle according to an operation being performed with the imaging needle apparatus;

an imager disposed inside of the probe, the imager including a plurality of photocells; and a control mechanism provided on the body, the control mechanism having a first state and a second state; and a display displaying an image based on the imaging signal, wherein the blunt tip is configured to be retracted to be housed within the needle body when the control mechanism is in the first state and extended from the needle and exposed when the control mechanism is in the second state, and wherein the control mechanism includes a plurality of fins extending from the body, the plurality of fins being configured to rotate in a circumferential direction.

12. The system of claim 11, wherein the needle is hollow, the probe being disposed inside of the needle body.

13. The system of claim 11, wherein the body includes a syringe configured to exert a pressure in a space inside of the probe.

14. The system of claim 13, wherein the probe has a plurality of side ports and a plurality of lumens, the side ports being holes through a side of the probe, the lumens being holes through the blunt tip of the probe, and wherein when the syringe body exerts a pressure on a fluid in the space, the fluid is emitted through the side ports and the lumens.

15. The system of claim 11, further comprising:

a lens assembly disposed inside of the probe, the lens assembly including a plurality of lenses respectively focusing light on the plurality of photocells of the imager; and a plurality of illumination light pipes extending along an outer surface of the imager and an outer surface of the lens assembly, the plurality of illumination light pipes transmitting light through the blunt tip of the probe, wherein the imager includes an imager chip and a stack of integrated circuits (ICs) coupled to the imager chip, the imager chip including the plurality of photocells arrayed in a grid, the stack of ICs processing imaging signals from the photocells of the imager.

* * * * *